US006794397B2

(12) United States Patent
Cai et al.

(10) Patent No.: US 6,794,397 B2
(45) Date of Patent: Sep. 21, 2004

(54) SUBSTITUTED NICOTINAMIDES AND ANALOGS AS ACTIVATORS OF CASPASES AND INDUCERS OF APOPTOSIS AND THE USE THEREOF

(75) Inventors: Sui Xiong Cai, San Diego, CA (US); John A. Drewe, Carlsbad, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/769,420

(22) Filed: Jan. 26, 2001

(65) Prior Publication Data

US 2002/0010185 A1 Jan. 24, 2002

Related U.S. Application Data

(60) Provisional application No. 60/177,648, filed on Jan. 27, 2000.

(51) Int. Cl.$^7$ .................. C07D 213/82; A61K 31/44; A61K 31/455; A61P 35/00; A61P 35/02
(52) U.S. Cl. .................. 514/344; 514/350; 514/352; 514/355; 546/286; 546/297; 546/298; 546/310; 546/316
(58) Field of Search ................ 514/344, 350, 514/352, 355; 546/286, 298, 297, 310, 316

(56) References Cited

U.S. PATENT DOCUMENTS

| | | | |
|---|---|---|---|
| 3,406,168 A | | 10/1968 | Schmidt .................. 260/239.3 |
| 4,261,730 A | | 4/1981 | Bollinger et al. .............. 71/94 |
| 4,978,385 A | * | 12/1990 | Yagihara et al. ................ 71/94 |
| 4,987,140 A | * | 1/1991 | Clemence et al. .......... 514/335 |
| 5,340,827 A | * | 8/1994 | Beeley et al. ................ 514/352 |
| 5,455,348 A | * | 10/1995 | Austel et al. ................ 544/238 |
| 5,635,519 A | * | 6/1997 | Okamoto et al. ........... 514/333 |
| 5,703,075 A | * | 12/1997 | Gammill et al. ......... 514/233.5 |
| 6,022,884 A | * | 2/2000 | Mantlo et al. .............. 514/352 |
| 6,028,111 A | | 2/2000 | Pero et al. .................. 514/620 |
| 2003/0004189 A1 | * | 1/2003 | Cutshall et al. ............. 514/336 |

FOREIGN PATENT DOCUMENTS

| | | |
|---|---|---|
| DE | 3804346 A1 * | 8/1989 |
| EP | 0 807 633 A2 | 11/1997 |
| FR | 2636329 A2 * | 3/1990 |
| GB | 1 573 576 | 8/1980 |
| JP | 06263702 A2 * | 9/1994 |
| JP | 10/291988 A2 * | 11/1998 |
| JP | 2000-256358 | 9/2000 |
| WO | WO 95/25723 | 9/1995 |
| WO | WO 96/20721 | 7/1996 |
| WO | WO 99/19303 A1 * | 4/1999 |
| WO | 99/19303 A1 * | 4/1999 |
| WO | WO 99/24404 | 5/1999 |
| WO | WO 99/36391 | 7/1999 |
| WO | 99/51587 A1 * | 10/1999 |
| WO | WO 00/04901 | 2/2000 |
| WO | WO 00/06550 | 2/2000 |
| WO | WO 00/44216 | 8/2000 |
| WO | WO 00/55114 | 9/2000 |
| WO | WO 00/62778 | 10/2000 |
| WO | WO 01/02354 | 1/2001 |
| WO | WO 01/21598 | 3/2001 |

OTHER PUBLICATIONS

Setliff, Frank L.; Soman, Nikhil G.; Caldwell, Jody Z.; Rogers, Debra L., Proceedings of the Arkansas Academy of Science, 46, 72–4 (English) 1992.*
Persons, Cecil C.; Shaikh, Ali U.; Shiflett, Julie; Setliff, Frank L., Proceedings of the Arkansas Academy of Science, 48, 130–2 (English) 1994.*
Setliff, Frank L.; Hawley, John W.; Toland, Alan D. Proceedings of the Arkansas Academy of Science, 49, 166–168 (English) 1995.*
Klebanov, B.M.; Ryabukha, T.K.; Miryan, N. I.; Fadeicheva, A. G.; Fialkov, Yu. A.; Driga, S. V., Fiziologicheski Aktivnye Veshchestva, 10, 21–3 (Russian) 1978.*
Bukhtiarova, T. A.; Trinus, F. P.; Danilenko, V. F.; Danilenko, G. I.; Ovrutskii, V. M.; Sharykina, N. I., Khimiko–Farmatsevtiches Zhurnal, 31(11), 30–32 (Russian) 1997.*
PTO–03–5414, translation of Bukhtiarova, T. A.; Trinus, F. P.; Danilenko, V. F.; Danilenko, G. I.; Ovrutskii, V. M.; Sharykina, N. I., Khimiko–Farmatsevticheskii Zhurnal, 31(11), 30–32 (Russian) 1997.*
Miryan, N. I.; Endel'man, E. S.; Klebanov, B. M.; Fadeicheva, A. G.; Ryabukha, T. K.; Driga, S. V.; Fialkov, Yu. A., Khimiko–Farmatsevticheskii Zhurnal, 11(1), 70–2 (Russian) 1977.*

(List continued on next page.)

*Primary Examiner*—James O. Wilson
*Assistant Examiner*—Thomas McKenzie
(74) *Attorney, Agent, or Firm*—Sterne, Kessler, Goldstein & Fox P.L.L.C.

(57) ABSTRACT

The present invention is directed to substituted nicotinamides and analogs thereof, represented by Formula V:

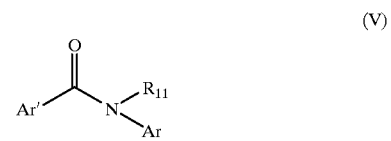

(V)

or a pharmaceutically acceptable salt or prodrug thereof, wherein:
Ar' and Ar are independently optionally substituted aryl or optionally substituted heteroaryl, provided that the ring structure of said optionally substituted heteroaryl comprises not more than two nitrogen atoms; and
$R_{11}$ is hydrogen; or alkyl, cycloalkyl, aryl or heteroaryl, each of which is optionally substituted.

The present invention also relates to the discovery that compounds having Formula V are activators of caspases and inducers of apoptosis. Therefore, the compounds of this invention may be used to induce cell death in a variety of clinical conditions in which uncontrolled growth and spread of abnormal cells occurs.

25 Claims, 5 Drawing Sheets

OTHER PUBLICATIONS

PTO 03–5440, translation of Koichi (JP 6/263,702).*
PTO 03–0105, translation of Kubota (WO 99/19303 A1).*
Setliff, Frank, L.; Soman, Nikhil G.; Caldwell, Jody Z.; Rogers, Debra L., Proceedings of the Arkansas Academy of Science, 46, 72–4 (English) 1992. Chemical Abstracts 1994:106286.*
Persons, Cecil C.; Shaikh, Ali U.; Shiflett, Julie; Setliff, Frank L., Proceedings of the Arkansas Academy of Science, 48, 130–2 (English) 1994, Chemical Abstracts 1995:627455.*
Setliff, Frank L.; Hawley, John W.; Toland, Alan D. Proceedings of the Arkansas Academy of Science, 49, 166–168 (English) 1995, Chemical Abstracts, 1996:383392.*
Talanian, R.V. et al, Ann. Reports Med. Chem., vol. 33, 1998, pp. 273–282.*
Miller, D.K. Ann. Reports Med. Chem., vol. 31, 1996, pp. 249–266.*
Chemical Abstracts 1995:249040.*
Klebanov, B.M.; Ryabukha, T. K.; Miryan, N. I.; Fadeicheva, A. G.; Fialkov, Yu. A.; Driga, S. V., Fiziologicheski Aktivnye Veshchestva, 10, 21–3 (Russian) 1978., Chemical Abstracts 1979:8071.*
Bukhtiarova, T. A.; Trinus, F. P.; Danilenko, V. F.; Danilenko, G. I.; Ovrutskii, V. M.; Sharykina, N. I., Khimiko–Farmatsevtiches Zhurnal, 31(11), 30–32 (Russian) 1997 Chemical Abstracts 128:289722.*
Miryan, N. I.; Endel'man, E. S.; Klebanov, B. M.; Fadeicheva, A. G.; Ryabukha, T. K.; Driga, S. V.; Fialkov, Yu. A., Khimiko–Farmatsevticheskii Zhurnal, 11(1), 70–2 (Russian) 1977, Chemical Abstracts 86:139798.*
Stedman's (Medical Dictionary, 27th Ed.), Williams & Wilkins, Baltimore, 2000.*
Setliff, Frank L.; Caldwell, Jody Z., Proc. Arkansas Acad. Sci., 45, 92–4 (English) 1991.*
Translation of Kubota (WO 99/19303 A1), PTO–03–0105 document, Nov., 2001.*
Salmon, S.E. et al "Principles of Cancer Therapy" in "Cecil Textbook of Medicine, 20th Edition", W.B. Saunders, Philadelphia, 1996, pp. 1036–1049.*
Balasubramanian, B.N. et al, "Recent Developments in Cancer Cytoxics" in "Annual Reports in Medicinal Chemistry, vol. 33", Academic Press, San Diego, 1998, pp. 151–159.*
Miller, D.M. "The Future of Oncology" in "Cecil Textbook of Medicine, 20th Edition", W.B. Saunders, Philadelphia, 1996, pp. 1071–1077.*
Setliff, Frank L.; Caldwell, Jody Z., Proc. Arkansas Acad. Sci., 45, 92–4 (English) 1991, CAS abstract 117:131027.*
Low, L.K. et al,. "Burger's Medicinal Chemistry, 4ed, Part I, Wolff, Manfred Ed.", John Wiley & Sons, 1980, pp. 175–178..*
Testa, B.,. "Burger's Medicinal Chemistry, 5ed, Part I, Wolff, Manfred Ed.", John Wiley & Sons, 1995, pp. 177–178..*
Draetta, G. and Pagano, M. in "Annual Reports in Medicinal Chemistry, vol. 31", 1996, Academic Press, San Diego, pp. 241–246.*
Setliff, Frank L.; Caldwell, Jody Z., Proc. Arkansas Acad. Sci., 45, 92–4 (English) 1991.*
Ruddon, R.W., "Biochemistry of Cancer," in *Cancer Medicine*, Bast, R.C., et al., eds., B.C. Decker, Inc., Hamilton, Ontario, section 1.7, (2000).

Atwell, G.J. et al., "Potential Antitumor Agents. VII. Bisquaternary Salts," *J. Med. Chem.* 11:300–305, American Chemical Society (1968).
Balcells, M. et al., "Synthesis of Phenoxyphenyl Pyridine and Pyrazine Carboxamides. Activity against *Cydia pomonella* (L.) Eggs," *J. Agric. Food Chem.* 48:83–87, American Chemical Society (2000).
Cooper, G.H. and Richard, R.L., "Reductive Acylation of 5–Nitropyridines with Anhydrides of Acetic, Phthalic, and Succinic Acids," *J. Chem. Soc. C 19*:3257–3260, Chemical Society (1971).
Doležal, M. et al., "Synthesis and Antimycobacterial, Antifungal, and Photosynthesis–Inhibiting Evaluation of Some Anilides of Substituted Pyrazine–2–carboxylic Acids," *Chem. Papers 54*:245–248, Slovak Academy of Sciences (2000).
Doležal, M. et al., "Synthesis and Photosynthesis–Inhibiting Activity of Some Anilides of Substituted Pyrazine–2–carboxylic Acids," *Chem. Papers 53*:126–130, Veda (1999).
Liégeois, J.–F. F. et al., "New Pyridobenzodiazepine Derivatives as Potential Antipsychotics: Synthesis and Neurochemical Study," *J. Med. Chem.* 36:2107–2114, American Chemical Society (1993).
Palanki, M.S.S. et al., "Inhibitors of NF–κB and AP–1 Gene Expression: SAR Studies on the Pyrimidine Portion of 2–Chloro–4–trifluoromethylpyrimidine–5– [N–(3',5'–bis (trifluoromethyl)–phenyl)carboximade],"*J. Med. Chem.* 43:3995–4004, American Chemical Society (2000).
White, G.A., "Substituted 2–Methylbenzanilides and Structurally Related Carboxamides: Inhibition of Complex II Activity in Mitochondria from a Wild–Type Strain and a Carboxin–Resistant Mutant Strain of *Ustilago maydis,*" *Pest. Biochem. Physiol. 34*:255–276, Academic Press, Inc. (1989).
International Search Report for International patent application No. PCT/US01/02478, mailed May 31, 2001.
Batteux, F. et al., "Gene Therapy of Experimental Autoimmune Thyroiditis by In Vivo Administration of Plasmid DNA Coding for Fas Ligand," *J. Immunol. 162*:603–608, The American Association of Immunologists (Jan. 1999).
Boirivant, M. et al., "*Lamina propria* T Cells in Crohn's Disease and Other Gastrointestinal Inflammation Show Defective CD2 Pathway–Induced Apoptosis," *Gastroenterol. 116*:557–565, American Gastroenterological Association (Mar. 1999).
Coven, T.R. et al., "PUVA–induced lymphocyte apoptosis: Mechanism of action in psoriasis," *Photodermatol. Phytoimmunol. Photomed. 15*:22–27, Munksgaard (Feb. 1999).
Ellis, R.E. et al., "Mechanisms and Functions of Cell Death," *Annu. Rev. Cell. Biol. 7*:663–698, Annual Reviews, Inc. (1991).
Friesen, C. et al., "Involvement of the CD95 (APO–1/Fas) receptor/ligand system in drug–induced apoptosis in leukemia cells," *Nature Med.2*:574–577, Nature Publishing Group (1996).
Greenwald, R.B. et al., "Drug Delivery Systems Employing 1,4– or 1,6–Elimination: Poly(ethylene glycol) Prodrugs of Amine–Containing Compounds," *J. Med. Chem.* 42:3657–3667, American Chemical Society (Sep. 1999). (Published on Web, Aug. 13, 1999).
Heenen, M. et al., "Methotrexate induces apoptotic cell death in human keratinocytes," *Arch. Dermatol. Res.* 290:240–245, Springer–Verlag (1998).

Infante, A.J. et al., "The clinical spectrum in a large kindred with autoimmune lymphoproliferative syndrome caused by a Fas mutation that impairs lymphocyte apoptosis," *J. Pediatr. 133*:629–633, (1998).

Leu, Y.-L. et al., "Design and Synthesis of Water–Soluble Glucuronide Derivatives of Camptothecin for Cancer Prodrug Monotherapy and Antibody–Directed Enzyme Prodrug Therapy (ADEPT)," *J. Med. Chem. 42*:3623–3628, American Chemical Society (Sep. 1999). (Published on Web, Aug. 24, 1999).

López–Hoyos, M. et al., "Regulation of B cell apoptosis by Bcl–2 and Bcl–$X_L$ and its role in the development of autoimmune diseases (Review)," *Int. J. Mol. Med. 1*:475–483, D.A. Spandidos (1998).

Los, M. et al., "Cross–Resistance of CD95– and Drug–Induced Apoptosis as a Consequence of Deficient Activation of Caspases (ICE/Ced–3 Proteases)," *Blood 90*:3118–3129, The American Society of Hematology (1997).

O'Reilly, L.A. and A. Strasser, "Apoptosis and autoimmune disease," *Inflamm. Res. 48*:5–21, Birkäuser Verlag (Jan. 1999).

Ohsako, S. and K.B. Elkon," Apoptosis in the effector phase of autoimmune diabetes, multiple sclerosis and thyroiditis," *Cell Death Differ. 6*:13–21, Stockton Press (Jan. 1999).

Orrenius, S., "Apoptosis: molecular mechanisms and implications for human disease," *J. Internal Med. 237*:529–536, Blackwell Science Ltd. (1995).

Ozawa, M. et al., "312–nanometer Ultraviolet B Light (Narrow–Band UVB) Induces Apoptosis of T Cells within Psoriatic Lesions," *J. Exp. Med. 189*:711–718, The Rockefeller University Press (Feb. 1999).

Savill, J., "Apoptosis in resolution of inflammation," *J. Leukocyte Biol. 61*:375–380, Society for Leukocyte Biology (1997).

Schmitt, E. et al., "The Bcl–xL and Bax–α control points: modulation of apoptosis induced by cancer chemotherapy and relation to TPCK–sensitive protease and caspase activation," *Biochem. Cell Biol. 75*:301–314, NCR Canada (1997).

Thornberry, N.A., "The caspase family of cysteine proteases," *Br. Med. Bull. 53*:478–490, The British Council (1997).

Thornberry, N.A., "Caspases: key mediators of apoptosis," *Chemistry & Biology 5*:R97–R103, Current Biology Ltd. (1998).

Vaishnaw, A.K. et al., "The molecular basis from apoptotic defects in patients with CD95 (Fas/Apo–1) mutations," *J. Clin. Invest. 103*:355–363, American Society for Clinical Investigation (Feb. 1999).

Wakisaka, S. et al., "Modulation by proinflammatory cytokines of Fas/Fas ligand–mediated apoptotic cell death of synovial cells in patients with rheumatoid arthritis (RA)," *Clin. Exp. Immunol. 114*:119–128, Blackwell Science (1998).

Wyllie, A.H., "Cell death: a new classification separating apoptosis from necrosis," in *Cell death in biology and pathology*, Bowen, I.D. and R.A. Lockshin, eds., Chapman and Hall, 1981, pp. 9–34.

Wyllie, A.H. et al., "Cell Death: The Significance of Apoptosis," *Intl. Rev. Cytol. 68*:251–306, Academic Press, Inc. (1980).

Zhou, T. et al., "Bisindolymaleimide VIII facilitates Fas-–mediated apoptosis and inhibits T cell–mediated autoimmune diseases," *Nature Med. 5*:42–48, Nature Publishing Group (Jan. 1999).

* cited by examiner

| Marker | % |
|---|---|
| All | 100.0 |
| M1 | 2.6 |
| M2 | 42.4 |
| M3 | 3.8 |
| M4 | 34.8 |
| M5 | 9.8 |

| Marker | % |
|---|---|
| All | 100.0 |
| M1 | 25.1 |
| M2 | 7.4 |
| M3 | 5.3 |
| M4 | 57.2 |
| M5 | 3.8 |

| Marker | % |
|---|---|
| All | 100.0 |
| M1 | 3.3 |
| M2 | 68.4 |
| M3 | 6.1 |
| M4 | 16.5 |
| M5 | 5.5 |

| MarKe | % |
|---|---|
| Al | 100.0 |
| M1 | 56.1 |
| M2 | 13.7 |
| M3 | 4.3 |
| M4 | 18.5 |
| M5 | 7.3 |

SUBSTITUTED NICOTINAMIDES AND ANALOGS AS ACTIVATORS OF CASPASES AND INDUCERS OF APOPTOSIS AND THE USE THEREOF

CROSS REFERENCE TO RELATED APPLICATIONS

This application claims the benefit of U.S. Provisional Application No. 60/177,648, filed Jan. 27, 2000, the contents of which are entirely incorporated by reference herein.

BACKGROUND OF THE INVENTION

1. Field of the Invention

This invention is in the field of medicinal chemistry. In particular, the invention relates to substituted nicotinamides and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis, et al., *Dev.* 112:591–603 (1991); Vaux, et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

It has been found that a group of proteases are a key element in apoptosis (see, e.g., Thornberry, *Chemistry and Biology* 5:R97–R103 (1998); Thornberry, *British Med. Bull.* 53:478–490 (1996)). Genetic studies in the nematode *Caenorhabditis elegans* revealed that apoptotic cell death involves at least 14 genes, two of which are the pro-apoptotic (death-promoting) ced (for cell death abnonnal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell Biol.* 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118–3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (See, e.g., Hardman, et al., eds., *Goodman and Gilman's The Pharmacological Basis of Therapeutics*, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

PCT published patent application WO95/25723 discloses anilide derivatives as fungicides:

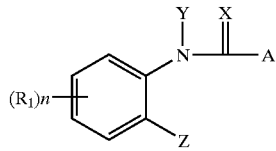

wherein,

X is O or S;

A is a 6 membered heteroaryl group comprising at least one nitrogen atom, which is optionally substituted by one or more of the group $R^2$;

$R^1$ is alkyl, cycloalkyl, cycloalkenyl, alkenyl, alkynyl, or amino, (each of which is optionally substituted), Y'—X—, halogen, cyano, nitro, acyl, acyloxy, optionally substituted heterocyclyl or optionally substituted phenyl; or two adjacent groups together with the carbon atoms to which they are attached can form an optionally substituted benzo ring;

$R^2$ is the same meaning as $R^1$ or two adjacent groups together with the carbon atoms to which they are attached can form an optionally substituted heterocyclic ring;

Y is alkyl, cycloalkyl, cycloalkenyl, alkenyl or alkynyl, each of which is optionally substituted, hydrogen or acyl;

$Y^1$ has the same meaning as Y or is optionally substituted phenyl or optionally substituted heterocyclyl;

Z is C(=X)—$X^2$—$R^3$, cyano, nitro, amino, acyl, optionally substituted heterocyclyl, —C($R^5$)=N—$OR^6$ or —C($R^5$)=N—$NR^6R^7$;

$R^3$ is alkyl, cycloalkyl, cycloalkenyl, alkenyl, alkynyl, phenyl or heterocyclyl, each of which is optionally substituted, hydrogen or an inorganic or organic cationic group;

X and $X^2$, which may be the same or different, are O or S;

$R^5$, $R^6$ and $R^7$, which may be the same or different, are alkyl, cycloalkyl, cycloalkenyl, alkenyl, alkynyl, phenyl or heterocyclyl, each of which is optionally substituted or hydrogen or $R^6$ and $R^7$ together with the atom(s) to which they are attached can form a ring;

and n is 0 to 4, together with complexes with metal salts, as well as salts with bases of compounds which are acids and salts with acids of compounds which are bases, with the proviso that when Y is hydrogen and i) when Z is carboxy, methoxycarbonyl or ethoxycarbonyl ring A is not unsubstututed pyridyl or pyrazinyl; and ii) when Z is carboxy and n is 0, A is not 2-chloro-3-pyridyl, 6-(2-diethylaminoethoxy)-3-pyridyl or a 2-pyridyl group.

PCT WO9936391 discloses benzenesulfonamide, benzamide, diarylsulfone and benzophenone compounds as pharmacological agents in the treatment of cancer, psoriasis, vascular restenosis, infections, atherosclerosis and hypercholesterolemia:

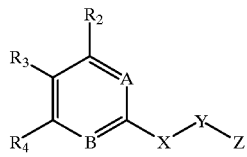

wherein, A represents N or C—$R^1$, B represents N or C—$R^5$; and $R^1$ and $R^5$ independently represent hydrogen, halogen, ($C_1$–$C_8$)alkyl, ($C_1$–$C_8$)heteroalkyl, —$OR^6$, —$NR^6R^7$, —S(O)$_m R^6$, —CN, —$NO_2$, —S(O)$_n NR^6R^7$ or —$N_3$; wherein $R^6$ and $R^7$ are independently selected from hydrogen, ($C_1$–$C_8$)alkyl, ($C_1$–$C_8$)heteroalkyl;

m is an integer of from 0 to 3;

n is an integer of from 1 to 2;

$R^2$ and $R^3$ are independently —$OR^8$, —$SR^8$, and —$NR^8R^9$, wherein $R^8$ and $R^9$ are independently hydrogen, ($C_1$–$C_6$)alkyl, ($C_1$–$C_6$)heteroalkyl;

$R^4$ is hydrogen, ($C_1$–$C_8$)alkyl, ($C_1$–$C_8$)heteroalkyl, —$OR^{10}$, —$SR^{10}$, or —$NR^{10}R^{11}$; wherein $R^{10}$ and $R^{11}$ are independently hydrogen, ($C_1$–$C_6$)alkyl, ($C_1$–$C_6$)heteroalkyl;

optionally, $R^1$ is linked to $R^2$ to form a fused ring, $R^2$ is linked to $R^3$ to form a fused ring, or $R^2$ is linked to both $R^1$ and $R^3$ to form two additional fused rings;

X represents —S(O)$_p$ or —C(O)—, wherein p is 1 or 2;

Y represents a single bond, —$CH_2$— or —N($R^{12}$)—, wherein $R^{12}$ is selected from hydrogen, ($C_1$–$C_6$)alkyl, ($C_1$–$C_6$)heteroalkyl and arylalkyl; and Z represents an aryl group or an arylalkyl group.

SUMMARY OF THE INVENTION

The present invention is related to the discovery that substituted nicotinamides and nicotinamide analogs as represented in Formula V are activators of the caspase cascade and inducers of apoptosis:

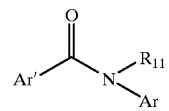

(V)

or a pharmaceutically acceptable salt or prodrug thereof, wherein:

Ar' and Ar are independently optionally substituted aryl or optionally substituted heteroaryl, provided that the ring structure of said optionally substituted heteroaryl comprises not more than two nitrogen atoms; and $R_{11}$ is hydrogen; or alkyl, cycloalkyl, aryl or heteroaryl, each of which is optionally substituted.

Thus, an aspect of the present invention is directed to the use of compounds of Formula V as inducers of apoptosis.

A second aspect of the present invention is to provide a method for treating, preventing or ameliorating neoplasia and cancer by administering a compound of Formula V to a mammal in need of such treatment.

Many of the compounds within the scope of the present invention are novel compounds. Therefore, a third aspect of the present invention is to provide novel compounds of Formula V, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula V in admixture with one or more pharmaceutically acceptable carriers or diluents.

A fifth aspect of the present invention is directed to methods for the preparation of novel compounds of Formula V.

BRIEF DESCRIPTION OF THE DRAWINGS

FIG. 1A depicts control cells. FIG. 1B depicts cells treated with 5 μM of N-(4-methoxy-2-nitrophenyl)-3-pyridinecarboxamide for 24 h, showing shrunken and fragmented nuclei.

FIG. 2 shows increasing percent of mitotic arrest with increasing drug concentration up to a concentration of 5 μM.

FIG. 3A: control cells showing most of the cells in G1(M2). FIG. 3B: cells treated with 10 μM of N-(4-methoxy-2-nitrophenyl)-3-pyridinecarboxamide for 48 h showing a reduction in the G1(M2), an increase in the G2/M (M4) and sub-diploid DNA content of cells (M1).

FIG. 4A: control cells showing most of the cells in G1(M2). FIG. 4B: cells treated with 1 μM of 6-chloro-N-(4-ethoxy-2-nitrophenyl)-3-pyridinecarboxamide for 48 h showing a reduction in the G1(M2), an increase in the G2/M (M4) and sub-diploid DNA content of cells (M1).

FIG. 5 shows that 6-chloro-N-(4-ethoxy-2-nitrophenyl)-3-pyridinecarboxamide inhibit colony formation of HeLa cells with an IC$_{50}$ of about 100 nM.

DETAILED DESCRIPTION OF THE INVENTION

Figure 1A:
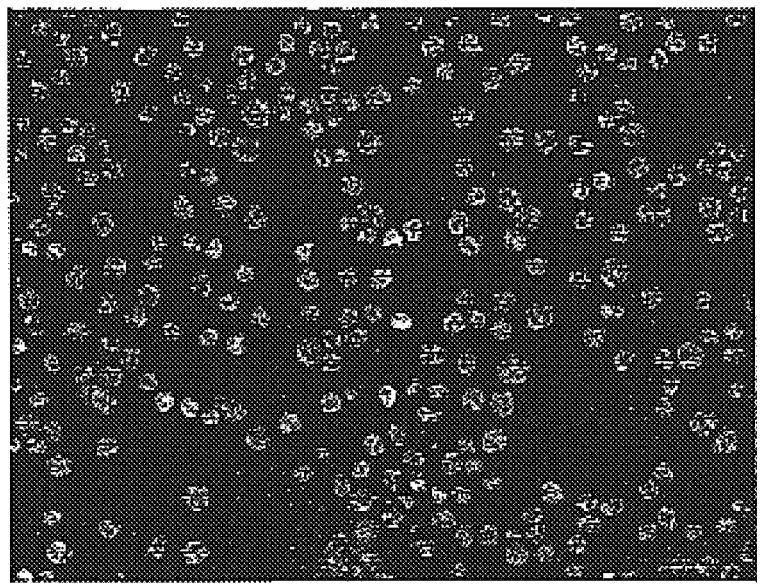
FIGS. 1A–B depict fluorescent micrographs of Jurkat cells as controls and as treated with drug and stained with a fluorescent DNA probe, Syto16.

The present invention arises out of the discovery that substituted nicotinamides and nicotinamide analogs, as represented in Formula V, are potent and highly efficacious activators of the caspase cascade and inducers of apoptosis:

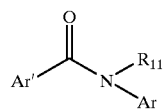

(V)

or a pharmaceutically acceptable salt or prodrug thereof, wherein:

Ar' and Ar are independently optionally substituted aryl or optionally substituted heteroaryl, provided that the ring structure of said optionally substituted heteroaryl comprises not more than two nitrogen atoms; and $R_{11}$ is hydrogen; or alkyl, cycloalkyl, aryl or heteroaryl, each of which is optionally substituted.

Therefore compounds of Formula V are useful for treating disorders responsive to induction of apoptosis.

Specifically, compounds useful in this aspect of the present invention are represented by Formula I:

(I)

or pharmaceutically acceptable salts or prodrugs thereof, wherein:

A is N or C—$R_8$; B is N or C—$R_9$, D is N or C—$R_{10}$, E is N or C—$R_6$, F is N or C—$R_7$, provided that not more than two of A, B, D, E, and F are N at the same time;

Ar is optionally substituted and is aryl or heteroaryl;

$R_6$–$R_{10}$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylamido, hydroxy, thiol, acyloxy, azido, alkoxy, alkoxycarbonyl, aryloxy, arylalkoxy, haloalkoxy, carboxy, carbonylamido or alkylthiol; and $R_{11}$ is hydrogen; or alkyl, cycloalkyl, aryl or heteroaryl, each of which is optionally substituted.

Preferred compounds of Formula I include compounds wherein Ar is optionally substituted phenyl, naphthyl, pyridyl, quinolyl, isoquinolyl, thienyl, furyl, or pyrrolyl. Preferred compounds of Formula I also include compounds wherein A is N, B is C—$R_9$, D is C—$R_{10}$, E is C—$R_6$ and F is C—$R_7$. Preferred compounds of Formula I also include compounds wherein A and D are N, B is C—$R_9$, E is C—$R_6$ and F is C—$R_7$. Preferred compounds of Formula I also include compounds wherein A and E are N, B is C—$R_9$, D is C—$R_{10}$ and F is C—$R_7$. Preferred compounds of Formula I also include compounds wherein $R_{11}$ is hydrogen.

Preferred structures of Formula I are substituted nicotinarnides and analogs represented by Formulae II–IV. In particular, a preferred embodiment is represented by Formula II:

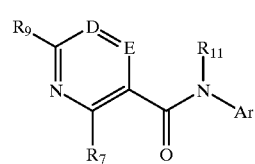

(II)

or pharmaceutically acceptable salts or prodrugs thereof, wherein $R_7$, $R_9$, $R_{11}$, D, E and Ar are as defined previously with respect to Formula I.

Preferred compounds falling within the scope of Formula II include compounds wherein Ar is optionally substituted phenyl or pyridyl. Preferred compounds of Formula II also include compounds wherein D is C—$R_{10}$ and E is C—$R_6$. Preferred compounds of Formula II also include compounds wherein D are N and E is C—$R_6$. Preferred compounds of Formula II also include compounds wherein E are N and D is C—$R_{10}$. Preferred compounds of Formula II also include compounds wherein $R_6$–$R_7$ and $R_{10}$ are independently hydrogen or fluoro.

Another preferred embodiment is represented by Formula III:

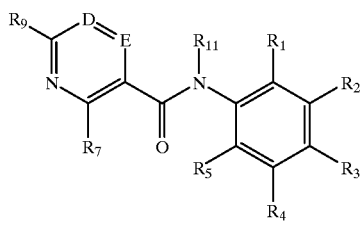

or pharmaceutically acceptable salts or prodrugs thereof, wherein $R_7$, $R_9$, $R_{11}$, D, and E are as defined previously with respect to Formula I;

$R_1$–$R_5$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylamido, hydroxy, thiol, acyloxy, azido, alkoxy, alkoxycarbonyl, aryloxy, arylalkoxy, haloalkoxy, carboxy, carbonylamido or alkylthiol; or $R_1$ and $R_2$, or $R_2$ and $R_3$, or $R_3$ and $R_4$, or $R_4$ and $R_5$ may be taken together to form a carbocycle or heterocycle, including —OCH$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —CH═CH—CH═CH—, —N(R)—CH═CH—, —CH═CH—N(R)—, —O—CH═CH—, —CH═CH—O—, —S—CH═CH—, —CH═CH—S—, —N═CH—CH═CH—, —CH═N—CH═CH—, —CH═CH—N═CH—, —CH═CH—CH═N— and —N═CH—CH═N—, wherein the carbocycle or heterocycle is optionally substituted, and R is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferred compounds falling within the scope of Formula III include compounds wherein D is C—$R_{10}$ and E is C—$R_6$. Preferred compounds of Formula II also include compounds wherein D are N and E is C—$R_6$. Preferred compounds of Formula II also include compounds wherein E are N and D is C—$R_{10}$. Preferred compounds of Formula II also include compounds wherein $R_6$–$R_7$ and $R_{10}$ are hydrogen or fluoro. Preferred compounds of Formula III also include compounds wherein $R_1$ and $R_3$ is not hydrogen. Preferred compounds of Formula III also include compounds wherein $R_2$ and $R_4$ are hydrogen or fluoro. Another group of preferred compounds of Formula III include compounds wherein $R_{11}$ is hydrogen.

Another preferred embodiment is represented by Formula IV:

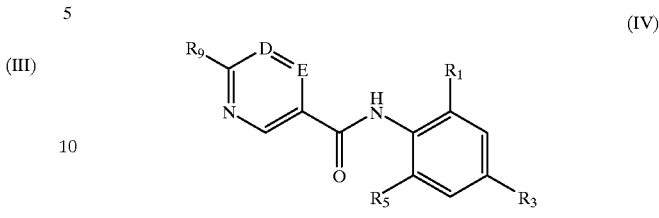

or pharmaceutically acceptable salts or prodrugs thereof, wherein $R_1$, $R_3$, $R_5$, $R_9$, D and E are as defined previously with respect to Formulae I and III.

Preferred compounds falling within the scope of Formula IV include compounds wherein D is C—$R_{10}$ and E is C—$R_6$. Preferred compounds of Formula II also include compounds wherein D are N and E is C—$R_6$. Preferred compounds of Formula II also include compounds wherein E are N and D is C—$R_{10}$. Preferred compounds of Formula IV also include compounds wherein $R_1$ and $R_3$ is not hydrogen. Especially preferred compounds of Formula IV include compounds wherein $R_1$ is nitro, cyano, trifluoromethyl and methyl. Especially preferred compounds of Formula IV also include compounds wherein $R_3$ is halo, haloalkyl, alkyl, amino, cyano, acyloxy, azido, alkoxy, aryloxy, arylalkoxy, haloalkoxy, or alkylthiol.

Another preferred embodiment is represented by Formula VI:

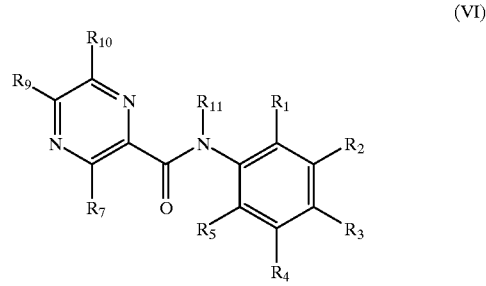

or a pharmaceutically acceptable salt or prodrug thereof, wherein $R_1$–$R_5$, $R_7$ and $R_9$–$R_{10}$ are independently hydrogen, halo, haloalkyl, haloalkoxy, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido or alkylthiol; and $R_{11}$ is hydrogen; or alkyl, cycloalkyl, aryl or heteroaryl, each of which is optionally substituted.

Another preferred embodiment is represented by Formula VII:

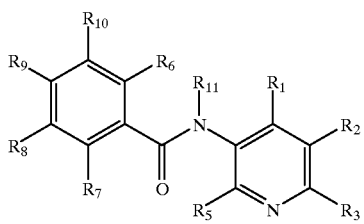

(VII)

or a pharmaceutically acceptable salt or prodrug thereof, wherein:

$R_1$–$R_3$, $R_5$–$R_{10}$ are are independently hydrogen, halo, haloalkyl, haloalkoxy, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido or alkylthiol; and $R_{11}$ is hydrogen; or alkyl, cycloalkyl, aryl or heteroaryl, each of which is optionally substituted.

Exemplary preferred compounds that may be employed in the method of the invention include, without limitation:

N-(4-Methoxy-2-nitrophenyl)-3-pyridinecarboxamide;
6-Chloro-N-(4-methoxy-2-nitrophenyl)-3-pyridinecarboxamide;
6-Chloro-N-(4-ethoxy-2-nitrophenyl)-3-pyridinecarboxamide;
6-Chloro-N-(4-methyl-2-nitrophenyl)-3-pyridinecarboxamide;
6-Chloro-N-(4-methoxy-2-nitrophenyl)-1-N-oxide-3-pyridinecarboxamide;
6-Chloro-N-(4-chloro-2-nitrophenyl)-3-pyridinecarboxamide;
6-Chloro-N-(4,5-difluoro-2-nitrophenyl)-3-pyridinecarboxamide;
6-Fluoro-N-(4-ethoxy-2-nitrophenyl)-3-pyridinecarboxamide;
6-Chloro-N-(4-fluoro-2-nitrophenyl)-3-pyridinecarboxamide;
6-Chloro-N-(2-nitro-4-trifluoromethylphenyl)-3-pyridinecarboxamide;
6-Chloro-N-(3-bromo-4-methoxy-6-nitrophenyl)-3-pyridinecarboxamide;
6-Chloro-N-(2-nitro-4-trifluoromethoxyphenyl)-3-pyridinecarboxamide;
6-Chloro-N-(4-benzyloxy-2-nitrophenyl)-3-pyridinecarboxamide;
6-Methyl-N-(4-ethoxy-2-nitrophenyl)-3-pyridinecarboxamide;
5,6-Dichloro-N-(4-methoxy-2-nitrophenyl)-3-pyridinecarboxamide;
6-Chloro-N-(2-methyl-4-methoxyphenyl)-3-pyridinecarboxamide;
6-Chloro-N-(4-cyano-2-nitrophenyl)-3-pyridinecarboxamide;
4-Chloro-N-(4-ethoxy-2-nitrophenyl)-benzoylamide;
6-Chloro-N-(4-ethoxy-2-nitrophenyl)-N-methyl-3-pyridinecarboxamide;
6-Chloro-N-(2-cyano-4,5-dimethoxyphenyl)-3-pyridinecarboxamide;
N-(4-Ethoxy-2-nitrophenyl)-3-pyridinecarboxamide;
N-(4-Methyl-2-nitrophenyl)-3-pyridinecarboxamide;
6-(2,2,2-Trifluoroethoxy)-N-(4-ethoxy-2-nitrophenyl)-3-pyridinecarboxamide;
N-(4-Ethoxy-2-nitrophenyl)-2-pyridinecarboxamide;
N-(4-Ethoxy-2-nitrophenyl)-5-pyridinecarboxamide;
6-Dimethylamino-N-(4-ethoxy-2-nitrophenyl)-3-pyridinecarboxamide;
6-Chloro-N-(4-t-butyl-2-nitrophenyl)-3-pyridinecarboxamide;
N-(4-Ethoxy-2-nitrophenyl)-1-N-oxide-2-pyridinecarboxamide;
6-Trifluoromethyl-N-(4-ethoxy-2-nitrophenyl)-3-pyridinecarboxamide;
6-Chloro-N-(4-chloro-2-trifluoromethylphenyl)-3-pyridinecarboxamide;
6-Methyl-N-(4-ethoxy-2-nitrophenyl)-3-pyrazinecarboxamide;
6-Chloro-N-(4-chloro-2-cyanophenyl)-3-pyridinecarboxamide;
N-(4-Ethoxy-2-nitrophenyl)-3-pyrazinecarboxamide;
6-Chloro-N-(2,4-dimethyl-6-nitrophenyl)-3-pyridinecarboxamide;
4-Chloromethyl-N-(4-ethoxy-2-nitrophenyl)-benzoylamide;
6-Chloro-N-(3,4-dimethoxy-6-nitrophenyl)-3-pyridinecarboxamide;
6-Chloro-N-(2-pyrazinyl)-3-pyridinecarboxamide;
6-Chloro-N-(1-N-oxide-3-cyano-5-chloromethyl-2-pyrazinyl)-3-pyridinecarboxamide;
6-Chloro-N-(2-cyano-4-methylphenyl)-3-pyridinecarboxamide;
6-Chloro-N-(4-chloro-2-methyl-6-nitrophenyl)-3-pyridinecarboxamide;
4-Trifluoromethyl-N-(4-ethoxy-2-nitrophenyl)-3-pyridinecarboxamide;
6-Chloromethyl-N-(4-ethoxy-2-nitrophenyl)-3-pyridinecarboxamide;
4-Chloro-2-nitro-N-(6-chloro-3-pyridyl)-benzoylainmide;
4-Chloro-2-nitro-N-(6-methoxy-3-pyridyl)-benzoylamide;
4-Bromomethyl-3-nitro-N-(6-chloro-3-pyridyl)-benzoylamide;
N-(4-Ethoxy-2-nitrophenyl)-3-furancarboxamide; and
N-(4-Ethoxy-2-nitrophenyl)-3-pyrrolecarboxamide.

The present invention is also directed to novel compounds within the scope of Formulae I–VII. In one preferred embodiment, the novel compounds of the present invention are compounds of Formula III:

(III)

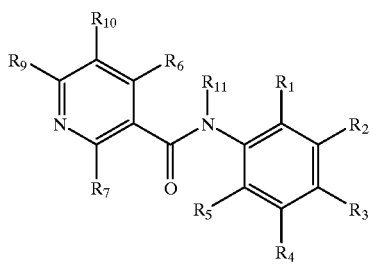

or pharmaceutically acceptable salts or prodrugs thereof, wherein:

$R_1$ and $R_5$ are independently selected from the group consisting of hydrogen, hydroxy, alkyl, alkoxy, halogen, $NO_2$, cyano, haloalkyl, haloalkoxy, amino and aminoalkyl, provided that at least one of $R_1$ and $R_5$ is selected from the group consisting of $NO_2$, cyano, alkyl and haloalkyl;

$R_2$ and $R_4$ are independently selected from the group consisting of hydrogen, hydroxy, halogen, cyano, haloalkyl, haloalkoxy, amino and aminoalkyl;

$R_3$ is alkyl, Cl, F, haloalkyl, alkoxy, arylalkoxy, cyano, haloalkyloxy, amino or aminoalkyl;

$R_6$ is hydrogen, hydroxy, alkyl, $NO_2$, cyano, haloalkyl, haloalkyloxy, amino or aminoalkyl;

$R_7$ is hydrogen, hydroxy, alkyl, $NO_2$, cyano, haloalkyl, haloalkyloxy, amino or aminoalkyl;

$R_9$ is hydroxy, alkyl, halogen, $NO_2$, haloalkyl, alkoxy, cyano, haloalkyloxy, amino or aminoalkyl;

$R_{10}$ is hydrogen, hydroxy, alkyl, Cl, F, $NO_2$, cyano, haloalkyl, haloalkyloxy, amino or aminoalkyl; and $R_{11}$ is hydrogen, alkyl or haloalkyl.

In a further preferred embodiment, the compounds of the present invention are compounds of Formula IV:

(IV)

or pharmaceutically acceptable salts or prodrugs thereof, wherein:

$R_3$ is alkyl, Cl, F, haloalkyl, alkoxy, arylalkoxy, cyano, haloalkyloxy, amino or aminoalkyl; and $R_9$ is hydroxy, alkyl, halogen, $NO_2$, haloalkyl, alkoxy, cyano, haloalkyloxy, amino or aminoalkyl.

In another preferred embodiment, the compounds of the present invention are compounds of Formula (VI):

(VI)

or pharmaceutically acceptable salts or prodrugs thereof, wherein $R_1$–$R_5$, $R_7$ and $R_9$–$R_{10}$ are independently hydrogen, halo, haloalkyl, haloalkoxy, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido or alkylthiol; and $R_{11}$ is hydrogen; or alkyl, cycloalkyl, aryl or heteroaryl, each of which is optionally substituted.

In another preferred embodiment, the novel compounds of the present invention are compounds of Formula (VII):

(VII)

or pharmaceutically acceptable salts or prodrugs thereof, wherein:

$R_1$–$R_3$, $R_5$–$R_{10}$ are independently hydrogen, halo, haloalkyl, haloalkoxy, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, aminoalkyl, cyano, cyanoalkyl, acyl, acylarnido, hydroxy, thiol, acyloxy, azido, alkoxy, alkoxycarbonyl, aryloxy, arylalkoxy, carboxy, carbonylamido or alkylthiol; and $R_{11}$ is hydrogen; or alkyl, cycloalkyl, aryl or heteroaryl, each of which is optionally substituted.

More preferably at least one of $R_6$ and $R_7$ selected from the group consisting of $NO_2$, cyano, alkyl and haloalkyl.

Exemplary preferred compounds of the present invention include, without limitation:

6-Chloro-N-(4-methoxy-2-nitrophenyl)-3-pyridinecarboxamide;

6-Chloro-N-(4-ethoxy-2-nitrophenyl)-3-pyridinecarboxamide;

6-Chloro-N-(4-methyl-2-nitrophenyl)-3-pyridinecarboxamide;

6-Chloro-N-(4-methoxy-2-nitrophenyl)-1-N-oxide-3-pyridinecarboxamide;

6-Chloro-N-(4-chloro-2-nitrophenyl)-3-pyridinecarboxamide;
6-Chloro-N-(4,5-difluoro-2-nitrophenyl)-3-pyridinecarboxamide;
6-Fluoro-N-(4-ethoxy-2-nitrophenyl)-3-pyridinecarboxamide;
6-Chloro-N-(4-fluoro-2-nitrophenyl)-3-pyridinecarboxamide;
6-Chloro-N-(4-trifluoromethyl-2-nitrophenyl)-3-pyridinecarboxamide;
6-Chloro-N-(3-bromo-4-methoxy-6-nitrophenyl)-3-pyridinecarboxamide;
6-Chloro-N-(2-nitro-4-trifluoromethoxy phenyl)-3-pyridinecarboxamide;
6-Chloro-N-(4-benzyloxy-2-nitrophenyl)-3-pyridinecarboxamide;
6-Methyl-N-(4-ethoxy-2-nitrophenyl)-3-pyridinecarboxamide;
5,6-Dichloro-N-(4-methoxy-2-nitrophenyl)-3-pyridinecarboxamide;
6-Chloro-N-(2-methyl-4-methoxyphenyl)-3-pyridinecarboxamide;
6-Chloro-N-(4-cyano-2-nitrophenyl)-3-pyridinecarboxamide;
4-Chloro-N-(4-ethoxy-2-nitrophenyl)-benzoylamide;
6-Chloro-N-(4-ethoxy-2-nitrophenyl)-N-methyl-3-pyridinecarboxamide;
6-Chloro-N-(2-cyano-4,5-dimethoxyphenyl)-3-pyridinecarboxamide;
6-(2,2,2-Trifluoroethoxy)-N-(4-ethoxy-2-nitrophenyl)-3-pyridinecarboxamide;
N-(4-Ethoxy-2-nitrophenyl)-2-pyridinecarboxamide;
N-(4-Ethoxy-2-nitrophenyl)-5-pyrimidinecarboxamide;
6-Dimethylamino-N-(4-ethoxy-2-nitrophenyl)-3-pyridinecarboxamide;
6-Chloro-N-(4-t-butyl-2-nitrophenyl)-3-pyridinecarboxamide;
N-(4-Ethoxy-2-nitrophenyl)-1-N-oxide-2-pyridinecarboxamide;
6-Trifluoromethyl-N-(4-ethoxy-2-nitrophenyl)-3-pyridinecarboxamide;
6-Chloro-N-(4-chloro-2-trifluoromethylphenyl)-3-pyridinecarboxamide;
6-Methyl-N-(4-ethoxy-2-nitrophenyl)-3-pyrazinecarboxamide;
6-Chloro-N-(4-chloro-2-cyanophenyl)-3-pyridinecarboxamide;
N-(4-Ethoxy-2-nitrophenyl)-3-pyrazinecarboxamide;
6-Chloro-N-(2,4-dimethyl-6-nitrophenyl)-3-pyridinecarboxamide;
4-Chloromethyl-N-(4-ethoxy-2-nitrophenyl)-benzoylamide;
6-Chloro-N-(3,4-dimethoxy-6-nitrophenyl)-3-pyridinecarboxamide;
6-Chloro-N-(2-pyrazinyl)-3-pyridinecarboxamide;
6-Chloro-N-(1-N-oxide-3-cyano-5-chloromethyl-2-pyrazinyl)-3-pyridinecarboxamide;
6-Chloro-N-(2-cyano-4-methylphenyl)-3-pyridinecarboxamide;
6-Chloro-N-(4-chloro-2-methyl-6-nitrophenyl)-3-pyridinecarboxamide;
4-Trifluoromethyl-N-(4-ethoxy-2-nitrophenyl)-3-pyridinecarboxamide;
6-Chloromethyl-N-(4-ethoxy-2-nitrophenyl)-3-pyridinecarboxamide;
4-Chloro-2-nitro-N-(6-chloro-3-pyridyl)-benzoylamide;
4-Chloro-2-nitro-N-(6-methoxy-3-pyridyl)-benzoylamide; and
4-Bromomethyl-3-nitro-N-(6-chloro-3-pyridyl)-benzoylamide.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

Useful alkoxy groups include oxygen substituted by one of the $C_{1-10}$ alkyl groups mentioned above, which may be optionally substituted.

Useful alkylthio groups include sulphur substituted by one of the $C_{1-10}$ alkyl groups mentioned above, which may be optionally substituted. Also included are the sulfoxides and sulfones of such alkylthio groups.

Useful amino groups include —$NH_2$, —$NHR_{15}$ and —$NR_{15}R_{16}$, wherein $R_{15}$ and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl ($C_2$–$C_6$)alkynyl, saturated and unsaturated heterocyclic or heteroaryl.

Optional substituents on the aryl, aralkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$) alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylakyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl) aminomethane (TRIS, tromethane) and N-methylglucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof such as succinic and fumaric anhydrides according to methods known in the art); imines of amino containing compounds (e.g., those obtained by condensation with a $C_{1-4}$ aldehyde or ketone according to methods known in the art); carbamate of amino containing compounds such as those described by Leu, et. al., (*J. Med. Chem.* 42:3623–3628 (1999)) and Greenwald, et. al., (*J. Med. Chem.* 42:3657–3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I–VII may be prepared as illustrated by the exemplary reaction in Scheme 1. Reaction of an acyl chloride with an amine in the presence a base such as triethylamine or N,N-diisopropylethylamine produces the amide.

Scheme 1

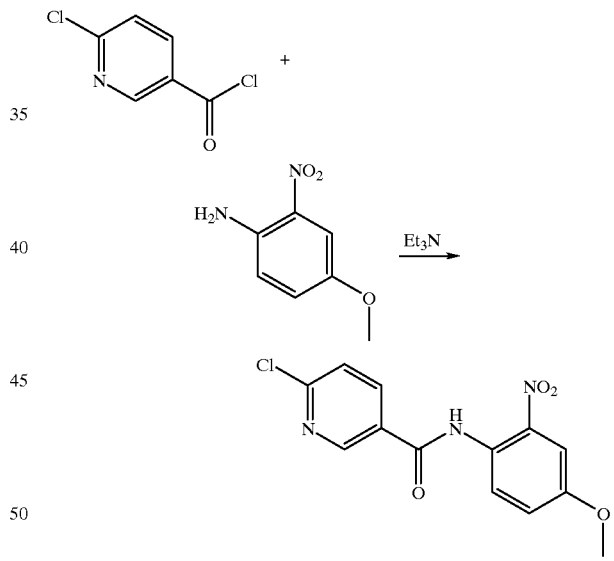

Alternatively, reaction of an acid with an amine in the presence of a coupling reagent such as EDC, or cyanuric chloride, also produces the amide as shown by the exemplary reaction in Scheme 2.

Scheme 2

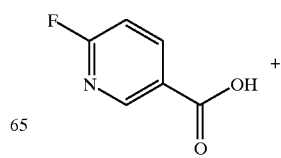

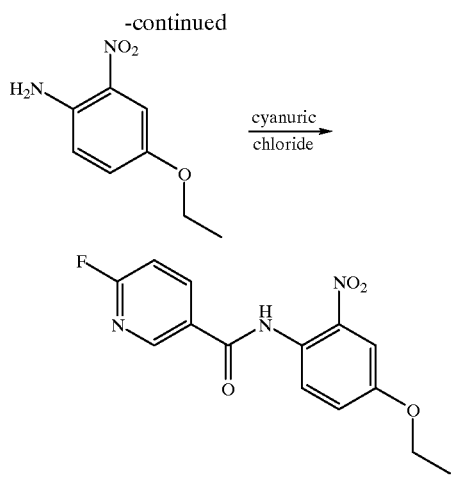

An important aspect of the present invention is the discovery that compounds having Formula I–VII are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formula I–VII are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–VII, which functions as a caspase cascade activator and inducer of apoptosis.

The present invention also includes a therapeutic method comprising administering to an animal an effective amount of a compound, or a pharmaceutically acceptable salt or prodrug of said compound of Formulae I–VII, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute lymphocytic leukemia, chronic lymphocytic leukemia, multiple myeloma, neuroblastoma, breast carcinomas, ovarian carcinomas, lung carcinomas, Wilms' tumor, cervical carcinomas, testicular carcinomas, soft-tissue sarcomas, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head or neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound, or a pharmaceutically acceptable salt of said compound of Formulae I–VII, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I–VII, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but not are limited to alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I–VII, which functions as a caspase cascade activator and inducer of apoptosis, in bioconjugation with at least one known therapeutically useful antibody, such as Herceptin® or Rituxan®, growth factors such as DGF, NGF, cytokines such as IL-2, IL-4, or any molecule that binds to the cell surface. The antibodies and other molecules will deliver the compound of Formulae I–VII to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective in inhibiting neoplasia comprising a compound, or a pharmaceutically acceptable salt or prodrug of said compound of Formulae I–VII, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–VII, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629–633 (1998) and Vaishnaw, A. K., et al., *J. Clin. Invest.* 103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5–21 (1999)).

Fas—Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 5 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide vm is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42–48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I–VII, which functions as a caspase cascade activator and inducer of apoptosis, should be an effective treatment for autoimmune diseases.

Psoriasis is a chronic skin disease that is characterized by scaly red patches. Psoralen plus ultraviolet A (PUVA) is a widely used and effective treatment for psoriasis vulgaris and Coven, et al., *PhotodennatoL Photoimmunol. Photomed.* 15:22–27 (1999), reported that lymphocytes treated with psoralen 8-MOP or TMP and UVA, displayed DNA degradation patterns typical of apoptotic cell death. Ozawa, et al., *J. Exp. Med.* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I–VII, which functions as a caspase cascade activator and inducer of apoptosis, should be an effective treatment for psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119–128 (1998), found that although RA synovial cells could die via apoptosis through a Fas/FasL pathway, apoptosis of synovial cells was inhibited by proinflammatory cytokines present within the synovium. Wakisaka, et al., also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–VII, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375–380 (1997)). Boirivant, et al., *Gastroenterology* 116:557–565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–VII, which functions as a caspase cascade activator and inducer of apoptosis, should be an effective treatment for inflammation.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg of body weight, per day, or an equivalent amount of the pharmaceutically acceptable salt thereof, to a mammal being treated for apoptosis-mediated disorders. Preferably, about 0.01 to about 10 mg/kg of body weight is orally administered to treat or prevent such disorders. For intramuscular injection, the dose is generally about one-half of the oral dose. For example, a suitable intramuscular dose would be about 0.0025 to about 25 mg/kg of body weight, and most preferably, from about 0.01 to about 5 mg/kg of body weight. If a known cancer chemotherapeutic agent is also administered, it is administered in an amount that is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which may be used pharmaceutically. Preferably, the preparations, particularly those preparations which may be administered orally and which may be used for the preferred type of administration, such as tablets, dragees, and capsules, and also preparations which may be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, poly-ethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or cremophor, or cyclodextrins. Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments, gels and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

The following examples are illustrative, but not limiting, of the method and compositions of the present invention.

Other suitable modifications and adaptations of the variety of conditions and parameters normally encountered in clinical therapy and which are obvious to those skilled in the art are within the spirit and scope of the invention.

EXAMPLE 1

6-Chloro-N-(2-nitro-4-trifluoromethylphenyl)-3-pyridinecarboxamide

To a mixture of 6-chloronicotinoyl chloride (100 mg, 0.6 mmol) and 2-nitro-4-trifluoromethylaniline (117 mg, 0.6 mmol) in THF (10 ml) was added triethylamine (0.16 ml, 1.1 mmol). The mixture was stirred at room temperature overnight and then diluted with ethyl acetate. Water was added to dissolve the precipitate and the organic phase was separated and washed with water, then dried over anhydrous sodium sulfate. The product was purified by column chromatography to give the title compound as a pale yellow solid. $^1$H NMR (DMSO-$d_6$): 11.27 (s, 1H), 8.97 (d, J=2.7, 1H), 8.38–8.35 (m, 2H), 8.19 (d, J=8.4, 1H), 7.96 (d, J=8.7, 1H), 7.78 (d, J=8.1, 1H).

EXAMPLE 2

6-Chloro-N-(4-chloro-2-nitrophenyl)-3-pyridinecarboxamide

The title compound was prepared from 6-chloronicotinoyl chloride and 4-chloro-2-nitroaniline and was obtained as a yellow solid as described in Example 1. $^1$H NMR (DMSO-d6): 11.31 (s, 1H), 9.02 (d, J=2.4, 1H), 8.96 (d, J=9.3, 1H), 8.31 (d, J=2.4, 1H), 8.24–8.20 (m, 1H), 7.73–7.69 (m, 1H), 7.54 (d, J=8.4, 1H).

EXAMPLE 3

6-Chloro-N-(4-fluoro-2-nitrophenyl)-3-pyridinecarboxamide

The title compound was prepared from 6-chloronicotinoyl chloride and 4-fluoro-2-nitroaniline and was obtained as a yellow solid as described in Example 1. $^1$H NMR (DMSO-d6): 10.97 (s, 1H), 8.94 (d, J=2.7, 1H), 8.36–8.32 (m, 1H), 8.02–7.98 (m, 1H), 7.78–7.75 (m, 1H), 7.73–7.72 (m, 1H), 7.70 (d, J=1.5, 1H).

EXAMPLE 4

6-Chloro-N-(3-bromo-4-methoxy-6-nitrophenyl)-3-pyridinecarboxamide

The title compound was prepared from 6-chloronicotinoyl chloride and 3-bromo-4-methoxy-6-nitroaniline and was obtained as a yellow solid as described in Example 1. $^1$H NMR (DMSO-d6): 10.84 (s, 1H), 8.93 (d, J=2.4, 1H), 8.34–8.30 (m, 1H), 7.98 (s, 1H), 7.76 (d, J=8.4, 1H), 7.70 (s, 1H), 3.97 (s, 3H).

EXAMPLE 5

6-Chloro-N-(2,4-dimethoxyphenyl)-3-pyridinecarboxamide

The title compound was prepared from 6-chloronicotinoyl chloride and 2,4-dimethoxyaniline as described in Example 1. The reaction mixture was filtered to remove the precipitate and the filtrate was evaporated. The resulting solid was purified by $CH_2Cl_2$/hexane recrystallization to give a light purple solid in a yield of 59%. $^1$H NMR (DMSO-$d_6$): 9.77

(s, 1H), 8.93 (s, 1H), 8.35–8.31 (m, 1H), 7.68 (d, J=7.8, 1H), 7.46 (d, J=9.0, 1H), 6.67 (d, J=2.4, 1H), 6.57–6.53 (m, 1H), 3.80 (s, 3H), 3.78 (s, 3H).

EXAMPLE 6

2-Chloro-N-(4-methoxy-2-nitrophenyl)-3-pyridinecarboxamide

The title compound was prepared from 2-chloronicotinoyl chloride and 4-methoxy-2-nitroaniline and was obtained as a yellow solid as described in Example 1. $^1$H NMR (CDCl$_3$): 10.76 (s, 1H), 8.78 (d, J=9.3, 1H), 8.58–8.55 (m, 1H), 8.13–8.09 (m, 1H), 7.73 (d, J=3.0, 1H), 7.45–7.40 (m, 1H), 7.34–7.28 (m, 1H0, 3.90 (s, 3H).

EXAMPLE 7

6-Chloro-N-(4-methoxy-2-nitrophenyl)-3-pyridinecarboxamide

The title compound was prepared from 6-chloronicotinoyl chloride and 4-methoxy-2-nitroaniline and was obtained as a yellow solid as described in Example 1. $^1$H NMR (CDCl$_3$): 11.13 (s, 1H), 9.01 (d, J=2.7, 1H), 8.83 (d, J=9.3, 1H), 8.24–8.20 (m, 1H), 7.76 (d, J=2.7, 1H), 7.52 (d, J=8.7, 1H), 7.35–7.31 (m, 1H), 3.90 (s, 3H).

EXAMPLE 8

6-Chloro-N-(4-ethoxy-2-nitrophenyl)-3-pyridinecarboxamide

The title compound was prepared from 6-chloronicotinoyl chloride and 4-ethoxy-2-nitroaniline and was obtained as a yellow solid as described in Example 1. $^1$H NMR (CDCl$_3$): 11.13 (s, 1H), 9.01 (d, J=2.4, 1H), 8.82 (d, J=9.3, 1H), 8.24–8.20 (m, 1H), 7.74 (d, J=3.0, 1H), 7.51 (d, J=7.8, 1H), 7.34–7.30(m, 1H), 4.11 (q, J=6.9, 2H), 1.47 (t, J=6.9, 3H).

EXAMPLE 9

6-Chloro-N-(4-methyl-2-nitrophenyl)-3-pyridinecarboxamide

The title compound was prepared from 6-chloronicotinoyl chloride and 4-methyl-2-nitroaniline and was obtained as a yellow solid as described in Example 1. $^1$H NMR (CDCl$_3$): 11.29 (s, 1H), 9.02 (d, J=2.7, 1H), 8.81 (d, J=8.7, 1H), 8.24–8.21 (m, 1H), 8.11 (s, 1H), 7.58–7.50 (m, 2H), 2.44 (s, 3H).

EXAMPLE 10

6-Chloro-N-(2-nitrophenyl)-3-pyridinecarboxamide

The title compound was prepared from 6-chloronicotinoyl chloride and 2-nitroaniline and was obtained as a yellow solid as described in Example 1. $^1$H NMR (CDCl$_3$): 10.99 (s, 1H), 8.95–8.94 (m, 1H), 8.36–8.33 (m, 1H), 8.02–7.99 (m, 1H), 7.80–7.69 (m, 3H), 7.48–7.42 (m, 1H).

EXAMPLE 11

6-Chloro-N-(4-methoxyphenyl)-3-pyridinecarboxamide

The title compound was prepared from 6-chloronicotinoyl chloride and p-anisidine and was obtained as a white solid as described in Example 1. $^1$H NMR (CDCl$_3$): 8.85 (d, J=2.1, 1H), 8.19–8.15 (m, 1H), 7.65 (s, 1H), 7.54–7.46 (m, 3H), 6.96–6.91 (m, 2H), 3.83 (s, 3H).

EXAMPLE 12

2,6-Dichloro-N-(4-methoxy-2-nitrophenyl)-4-pyridinecarboxamide

The title compound was prepared from 2,6-dichloropyridine-4-carbonyl chloride and 4-methoxy-2-nitroaniline and was obtained as a yellow solid as described in Example 1. $^1$H NMR (CDCl$_3$): 11.12 (s, 1H), 8.78 (d, J=9.3, 1H), 7.77 (d, J=3.0, 1H), 7.75 (s, 2H), 7.35–7.31 (m, 1H), 3.91 (s, 3H).

EXAMPLE 13

2-Chloro-4trifluoromethyl-N-(4methoxy-2-nitrophenyl)-5-pyrimidinecarboxamide

The title compound was prepared from 2-chloro-4-(trifluoromethyl)pyrimidine-5-carbonyl chloride and 4-methoxy-2-nitroaniline and was obtained as a light yellow solid as described in Example 1. $^1$H NMR (CDCl$_3$): 10.52 (s, 1H), 9.04 (s, 1H), 8.68 (d, J=9.3, 1H), 7.76 (d, J=3.0, 1H), 7.35–7.31 (m, 1H), 3.91 (s, 3H).

EXAMPLE 14

N-(4-methoxy-2-nitrophenyl)-4-pyridinecarboxamide

The title compound was prepared from isonicotinoyl chloride and 4-methoxy-2-nitroaniline and was obtained as an orange yellow solid as described in Example 1. $^1$H NMR (CDCl$_3$): 10.79 (s, 1H), 8.83–8.81 (m, 2H), 7.85–7.83 (m, 2H), 7.61–7.55 (m, 2H), 7.40–7.36 (m, 1H), 3.87 (s, 3H).

EXAMPLE 15

2,6-Dichloro-N-(4-methoxy-2-nitrophenyl)-3-pyridinecarboxamide

To a solution of 2,6-dichloronicotinic acid (100 mg, 0.52 mmol) in CH$_2$Cl$_2$ (10 mL) was added cyanuric chloride (96 mg, 0.52 mmol). The mixture was stirred for half an hour, then 4-methoxy-2-nitroaniline (88 mg, 0.52 mmol) and triethylamine (0.1 mL, 0.72 mmol) were added. The resulting mixture was stirred at room temperature overnight and then diluted with ethyl acetate, washed with water. The organic phase was separated, dried over anhydrous Na$_2$SO$_4$, concentrated and purified by chromatography to give the title compound (40 mg, 22%) as a yellow solid. $^1$H NMR (DMSO-d$_6$): 10.84 (bs, 1H), 8.09 (d, J=7.8, 1H), 7.75 (d, J=7.8, 1H), 7.57–7.52 (m, 2H), 7.37–7.33 (m, 1H), 3.86 (s, 3H).

EXAMPLE 16

5,6-Dichloro-N-(4-methoxy-2-nitrophenyl)-3-pyridinecarboxamide

The title compound was prepared from 5,6-dichloronicotinic acid and 4-methoxy-2-nitroaniline and was obtained as a yellow solid as described in Example 15. $^1$H NMR (DMSO-d$_6$): 10.85 (bs, 1H), 8.88 (d, J=2.4, 1H), 8.59 (d, J=2.4, 1H), 7.58–7.54 (m, 2H), 7.39–7.35 (m, 1H), 3.87 (s, 3H).

EXAMPLE 17

6-Chloro-N-(2,4-dinitrophenyl)-3-pyridinecarboxamide

The title compound was prepared from 6-chloronicotinoyl chloride and 2,4-dinitroaniline and was obtained as a yellow solid as described in Example 1. $^1$H NMR (CDCl$_3$): 11.69 (bs, 1H), 9.28–9.23 (m, 2H), 9.06–9.05 (m, 1H), 8.61–8.57 (m, 1H), 8.28–8.24 (m, 1H), 7.59–7.56 (m, 1H).

EXAMPLE 18

4-Chloro-N-(4-ethoxy-2-nitrophenyl)-benzoylamide

The title compound was prepared from 4-chlorobenzoyl chloride and 4-ethoxy-2-nitroaniline and was obtained as a yellow solid as described in Example 1. $^1$H NMR (CDCl$_3$): 11.10 (bs, 1H), 8.86 (d, J=9.3, 1H), 7.93 (d, J=8.4, 2H), 7.73 (d, J=3.0, 1H), 7.51 (d, J=8.4, 2H), 7.32–7.27 (m, 1H), 4.1 1 (q, J=6.9, 2H), 1.46 (t, J=6.9, 3H).

EXAMPLE 19

6-Chloro-N-(4,5-difluoro-2-nitrophenyl)-3-pyridinecarboxamide

The title compound was prepared from 6-chloronicotinoyl chloride and 4,5-difluoro-2-nitroaniline and was obtained as a yellow solid as described in Example 1. $^1$H NMR (CDCl$_3$): 11.49 (bs, 1H), 9.04–8.97 (m, 2H), 8.25–8.19 (m, 2H), 7.56–7.53 (m, 1H).

EXAMPLE 20

6-Chloro-N-(4-methoxy-2-methylphenyl)-3-pyridinecarboxamide

The title compound was prepared from 6-chloronicotinoyl chloride and 4-methoxy-2-methylaniline and was obtained as a white solid as described in Example 1. $^1$H NMR (CDCl$_3$): 8.88 (bs, 1H), 8.19 (d, J=7.2, 1H), 7.61–7.47 (m, 3H), 6.81–6.79 (m, 2H), 3.81 (s, 3H), 2.30 (s, 3H).

EXAMPLE 21

6-Chloro-N-(4-cyano-2-nitrophenyl)-3-pyridinecarboxamide

The title compound was prepared from 6-chloronicotinoyl chloride and 4-amino-3-nitrobenzonitrile and was obtained as a light yellow solid as described in Example 1. $^1$H NMR (CDCl$_3$): 11.58 (s, 1H), 9.18 (d, J=8.7, 1H), 9.04 (d, J=2.4, 1H), 8.65 (d, J=2.1, 1H), 8.26–8.22 (m, 1H), 8.00–7.96 (m, 1H), 7.56 (d, J=9.0, 1H).

EXAMPLE 22

6-Fluoro-N-(4-ethoxy-2-nitrophenyl)-3-pyridinecarboxamide

To the solution of KMnO$_4$ (284 mg, 1.8 mmol) in H$_2$O (50 mL) was added 2-fluoro-5-methylpyridine (100 mg, 0.9 mmol) at room temperature. The reaction mixture was then heated to 100° C. for 4 h. The resulting precipitate was filtered and discarded. The aqueous solution was washed with 3:2, hexane: ethyl acetate (2×20 mL), acidified with 2N HCl, then extracted with ethyl acetate (3×20 mL). The organic extracts were combined and washed with H$_2$O and brine, dried over anhydrous Na$_2$SO$_4$. The solvent was evaporated in vacuo to give 6-fluoronicotinic acid (30 mg) as a white solid. The title compound was prepared from 6-fluoronicotinic acid and 4-ethoxy-2-nitroaniline as a yellow solid as described in Example 15. $^1$H NMR (CDCl$_3$): 11.09 (bs, 1H), 8.88 (d, J=2.4, 1H), 8.81 (d, J=9.3, 1H), 8.42–8.35 (m, 1H), 7.74 (d, J=3.3, 1H), 7.33–7.29 (m, 1H), 7.13–7.10 (m, 1H), 4.11 (q, J=7.2, 2H), 1.47 (t, J=7.2, 3H).

EXAMPLE 23

6-Chloro-N-(2-nitro-4-tifluoromethoxyphenyl)-3-pyridinecarboxamide

The title compound was prepared from 6-chloronicotinoyl chloride and 2-nitro-4-(trifluoromethoxy)aniline and was obtained as a yellow solid as described in Example 1. $^1$H NMR (CDCl$_3$): 11.33 (bs, 1H), 9.06 (d, J=9.3, 1H), 9.02 (d, J=2.7, 1H), 8.25–8.21 (m, 1H), 8.19 (d, J=2.7, 1H), 7.65–7.61 (m, 1H), 7.54 (d, J=8.4, 1H).

EXAMPLE 24

6-Chloro-N-(4-benzoyl-2-nitrophenyl)-3-pyridinecarboxamide

The title compound was prepared from 6-chloronicotinoyl chloride and 4-amino-3-nitrobenzophenone and was obtained as a yellow solid as described in Example 1. $^1$H NMR (CDCl$_3$): 11.61 (bs, 1H), 9.12 (d, J=8.7, 1H), 9.06 (d, J=2.4, 1H), 8.79 (d, J=1.8, 1H), 8.28–8.25 (m, 1H), 8.23–8.19 (m, 1H), 7.82–7.81 (m, 1H), 7.80–7.79 (m, 1H), 7.67–7.64 (m, 1H), 7.58–7.53 (m, 3H).

EXAMPLE 25

6-Chloro-N-(4-benzyloxy-2-nitrophenyl)-3-pyridinecarboxamide

The title compound was prepared from 6-chloronicotinoyl chloride and 4-benzyloxy-2-nitroaniline and was obtained as a yellow solid as described in Example 1. $^1$H NMR (CDCl$_3$): 11.13 (bs, 1H), 9.00 (d, J=3.0, 1H), 8.83 (d, J=9.3, 1H), 8.23–8.20 (m, 1H), 7.85 (d, J=3.0, 1H), 7.53–7.46 (m, 1H), 7.44–7.37 (m, 6H), 5.15 (s, 2H).

EXAMPLE 26

6-Methyl-N-(4-ethoxy-2-nitrophenyl)-3-pyridinecarboxamide

The title compound was prepared from 6-methylnicotinic acid and 4-ethoxy-2-nitroaniline and was obtained as a yellow solid as described in Example 15. $^1$H NMR (CDCl$_3$): 11.09 (s, 1H), 9.12 (d, J=2.1, 1H), 8.85 (d, J=9.3, 1H), 8.16–8.13 (m, 1H), 7.73 (d, J=3.0, 1H), 7.34–7.29 (m, 2H), 4.11 (q, J=6.9, 2H), 2.67 (s, 3H), 1.46 (t, J=6.9, 3H).

EXAMPLE 27

6-Chloro-N-(4,5-dimethyl-2-nitrophenyl)-3-pyridinecarboxamide

The title compound was prepared from 6-chloronicotinoyl chloride and 4,5-dimethyl-2-nitroaniline and was obtained as an orange solid as described in Example 1. $^1$H NMR (CDCl$_3$): 11.38 (s, 1H), 9.03 (d, J=2.1, 1H), 8.72 (s, 1H), 8.24–8.21 (m, 1H), 8.07 (s, 1H), 7.52 (d, J=8.7, 1H), 2.41 (s, 3H), 2.34 (s, 3H).

EXAMPLE 28

6-Chloro-N-(4-methoxy-2-nitrophenyl)-1-N-oxide-3-pyridinecarboxamide

To a stirred solution of 30% H$_2$O$_2$ (2 mL) was added trifluoroacetic anhydride (1 mL) dropwise at 0° C. The resulting solution was stirred at 0° C. for 30 min, then 6-chloro-N-(4-methoxy-2-nitrophenyl)-3-pyridinecarboxamide (30 mg, 0.0975 mmol) was added. The mixture was stirred at 90° C. for 30 min. The resulting yellow solution was cooled in an ice bath for 1 h. The precipitate was filtered, washed with $H_2O$ and MeOH, and dried to give 15 mg (0.0463 mmol, 47%) of the title compound as a yellow powder. $^1$H NMR (CDCl$_3$): 11.11 (s, 1H), 8.95–8.76 (m, 1H), 8.78 (d, J=9.3. 1H), 7.76 (d, J=3.0, 1H), 7.66–7.65 (m, 2H), 7.35–7.31 (m, 1H), 3.91 (s, 3H).

EXAMPLE 29

N-(4-Methoxy-2-nitrophenyl)-3-pyridinecarboxamide

The title compound was prepared from nicotinoyl chloride and 4-methoxy-2-nitroaniline and was obtained as an orange solid as described in Example 1. $^1$H NMR (DMSO-d$_6$): 10.74 (s, 1H), 9.10 (d, J=2.4, 1H), 8.80–8.78 (m, 1H), 7.62–7.54 (m, 3H), 7.39–7.35 (m, 1H), 3.87 (s, 3H).

EXAMPLE 30

6-Chloro-N-(4-ethoxy-2-nitrophenyl)-N-methyl-3-pyridinecarboxamide

To a solution of 6-chloro-N-(4-ethoxy-2-nitrophenyl)-3-pyridinecarboxamide (50 mg, 0.155 mmol) in DMF (2 ml) was added sodium methoxide (12 mg, 0.222 mmol) in DMF (1 ml) and the reaction mixture was stirred for 10 min. To the mixture was added iodomethane (22 mg, 0.155 mmol) slowly and the mixture was stirred for at room temperature for 3 h. It was diluted with ethyl acetate and washed with water and brine, dried over anhydrous sodium sulfate, and evaporated. The residue was purified by column chromatography to yield the titled compound as a light brown liquid. $^1$H NMR (CDCl$_3$): 8.17 (d, J=2.1, 1H), 7.68–7.65 (m, 1H), 7.35 (d, J=2.7, 1H), 7.21 (t, J=7.8, 2H), 7.10–7.06 (m, 1H), 4.08–4.01 (m, 2H), 3.40 (s, 3H), 1.44 (t, J=6.9, 3H).

EXAMPLE 31

2,5-Dimethyl-N-(4-ethoxy-2-nitrophenyl)-3-furancarboxamide

The title compound was prepared from 2,5-dimethyl-3-furoic acid and 4-ethoxy-2-nitroaniline as an orange solid as described in Example 15. $^1$H NMR (CDCl$_3$): 10.59 (s, 1H), 8.83 (d, J=9.0, 1H), 7.70 (d, J=3.0, 1H), 7.27–7.25 (m, 1H), 6.24 (s, 1H), 4.08 (q, J=6.9, 2H), 2.62 (s, 3H), 2.30 (s, 3H), 1.45 (t, J=6.9, 3H).

EXAMPLE 32

6-Chloro-N-(5-bromo-3-nitro-2-pyridyl)-3-pyridinecarboxamide

The title compound was prepared from 6-chloronicotinoyl chloride and 2-amino-5-bromo-3-nitropyridine as a light yellow solid as described in Example 1. $^1$H NMR (CDCl$_3$): 10.56 (s, 1H), 9.00 (d, J=2.7, 1H), 8.82 (d, J=2.1, 1H), 8.69 (d, J=2.1, 1H), 8.27–8.23 (m, 1H), 7.53 (d, J=8.1, 1H).

EXAMPLE 33

N-(4-Ethoxy-2-nitrophenyl)-2-pyrazinecarboxamide

The title compound was prepared from 2-pyrazinecarboxylic acid and 4-ethoxy-2-nitroaniline as a yellow solid as described in Example 15. $^1$H NMR (CDCl$_3$): 12.34 (s, 1H), 9.50 (d, J=1.2, 1H), 8.91 (d, J=9.0, 1H), 8.84 (d, J=2.4, 1H), 8.72–8.70 (m, 1H), 7.75 (d, J=3.0, 1H), 7.33–7.28 (m, 1H), 4.12 (q, J=6.9, 2H), 1.47 (t, J=6.9, 3H).

EXAMPLE 34

5-Methyl-N-(4-ethoxy-2-nitrophenyl)-2-pyrazinecarboxamide

The title compound was prepared from 2-methylpyrazine-5-carboxylic acid and 4-ethoxy-2-nitroaniline as a yellow solid as described in Example 15. $^1$H NMR (CDCl$_3$): 12.82 (s, 1H), 9.36 (s, 1H), 8.90 (d, J=9.6, 1H), 8.56 (d, J=1.0. 1H), 7.74 (d, J=2.7, 1H), 7.32–7.29 (m, 1H), 4.11 (q, J=6.9, 2H), 2.71 (s, 3H), 1.46 (t, J=6.9, 3H).

EXAMPLE 35

6-Chloro-N-(4-chloro-2-cyanophenyl)-3-pyridinecarboxamide

The title compound was prepared from 6-chloronicotinoyl chloride and 2-amino-5-chlorobenzonitrile as a white solid as described in Example 1. $^1$H NMR (CDCl$_3$): 8.96 (d, J=2.7, 1H), 8.53–8.50 (M, 1H), 8.24 (s, 1H), 8.19–8.15 (m, 1H), 7.67–7.63 (m, 2H), 7.54–7.51 (m, 1H).

EXAMPLE 36

6-Chloro-N-(4-chloro-2-amidophenyl)-3-pyridinecarboxamide

The title compound was prepared from 6-chloronicotinoyl chloride and 2-amino-5-chlorobenzamide as a white solid as described in Example 1. $^1$H NMR (DMSO-d$_6$): 8.91 (d, J=2.7, 1H), 8.62 (d, J=9.3, 1H), 8.55 (s, 1H), 8.30–8.27 (m, 1H), 8.04 (s, 1H), 8.01 (d, J=2.7, 1H), 7.78 (d, J=8.4, 1H), 7.69–7.66 (m, 1H).

EXAMPLE 37

6-Trifluoromethyl-N-(4-ethoxy-2-nitrophenyl)-3-pyridinecarboxamide

The title compound was prepared from 6-trifluoromethylnicotinic acid and 4-ethoxy-2-nitroaniline as a yellow solid as described in Example 15. $^1$H NMR (CDCl$_3$): 11.23 (s, 1H), 9.32 (d, J=3.6, 1H), 8.83 (d, J=9.3, 1H), 8.47–8.43 (m, 1H), 7.88 (d, J=8.1, 1H), 7.76 (d, J=3.0, 1H), 7.35–7.31 (m, 1H), 4.12 (q, J=6.9, 2H), 1.47 (t, J=6.9, 3H).

EXAMPLE 38

6-Chloro-N-(4-chloro-2-methoxycarbonylphenyl)-3-pyridinecarboxamide

The title compound was prepared from 6-chloronicotinoyl chloride and methyl 2-amino-5-chlorobenzoate as a white solid as described in Example 1. $^1$H NMR (CDCl$_3$): 12.13 (s, 1H), 9.06 (d, J=3.0, 1H), 8.86 (d, J=9.3, 1H), 8.29–8.25 (m, 1H), 8.08 (d, J=2.4, 1H), 7.60–7.57 (m, 1H), 7.50 (d, J=8.4, 1H), 3.99 (s, 3H).

EXAMPLE 39

5-Bromo-N-(4-ethoxy-2-nitrophenyl)-3-pyridinecarboxamide

The title compound was prepared from 5-bromonicotinic acid and 4-ethoxy-2-nitroaniline as a yellow solid as described in Example 15. $^1$H NMR (CDCl$_3$): 11.11 (s, 1H), 9.11 (d, J=2.1, 1H), 8.88 (d, J=1.8, 1H), 8.80 (d, J=9.3, 1H), 8.42 (t, J=2.1, 1H), 7.75 (d, J=2.7, 1H), 7.34–7.30 (m, 1H), 4.12 (q, J=6.9, 2H), 1.47 (t, J=6.9, 3H).

EXAMPLE 40

N-(4-Ethoxy-2-nitrophenyl)-2-pyridinecarboxamide N-oxide

The title compound was prepared from picolinic acid N-oxide and 4-ethoxy-2-nitroaniline as a yellow solid as described in Example 15. $^1$H NMR (DMSO-$d_6$): 8.57–8.54 (m, 1H), 8.40 (d, J=9.0, 1H), 8.37–8.33 (m, 1H), 7.76–7.75 (m, 2H), 7.61 (d, J=3.0, 1H), 7.43–7.39 (m, 1H), 4.14 (q, J=6.9, 2H), 1.36 (t, J=6.9, 3H).

EXAMPLE 41

4-Amino-3-nitrophenyl 6-Chloro-3-pyridinecarboxylate (A) and 6-Chloro-N-(4-hydroxy-2-nitrophenyl)-3-pyridinecarboxamide (B)

A mixture of 4-amino-3-nitrophenol (200 mg, 1.30 mmol), 6-chloronicotinoyl chloride (229 mg, 1.30 mmol) and N,N-diisopropylethylamine (200 ul) in THF (5 ml) was stirred overnight at room temperature. The resulting solid was collected by filtration, wash with hexane:ethyl acetate (1:1) and dried under vacuo to give compound A as an orange solid (14 mg). $^1$H NMR (DMSO-$d_6$): 9.08 (dd, J=8.0, 2.6 Hz, 1H), 8.47 (dd, J=2.6, 8.3 Hz, 1H), 7.97 (d, J=2.7 Hz, 1H), 7.78 (dd, J=0.8, 8.3 Hz, 1H), 7.55 (s, 2H), 7.45 (dd, J=2.7, 9 Hz, 1H), 7.10 (d, J=9.0 Hz, 1H). The filtrate was diluted with ethyl acetate (50 ml), washed with water (25 ml), aqueous saturated NaCl (25 ml) and dried over anhydrous sodium sulfate. The solution was concentrated in vacuo and the product was purified by column chromatography using hexane:ethyl acetate (3:1) to give the product B as a dark yellow solid (9 mg). $^1$H NMR (DMSO-$d_6$): 9.13 (d, J=2.4 Hz, 1H), 8.96 (d, J=2.4 Hz, 1H), 8.52 (dd, J=1.8, 8.7 Hz, 1H), 8.36 (dd, J=2.4, 8.4 Hz, 1H), 8.07 (s, 1H), 7.85–7.80 (m, 2H), 7.73 (d, J=8.4 Hz, 1H).

EXAMPLE 42

N-(4-Ethoxy-2-nitrophenyl)-3-pyrrolecarboxamide

The title compound was prepared from pyrrole-3-carboxylic acid and 4-ethoxy-2-nitroaniline as a yellow solid as described in Example 15. $^1$H NMR (CDCl$_3$): 10.82 (s, 1H), 8.88 (d, J=9.3, 1H), 8.65 (s, 1H), 7.70 (d, J=3.0, 1H), 7.54–7.52 (m, 1H), 7.28–7.24 (m, 1H), 6.87–6.85 (m, 1H), 6.71–6.69 (m, 1H), 4.08 (q, J=6.9, 2H), 1.45 (t, J=6.9, 3H).

EXAMPLE 43

6-Chloro-N-(2-nitro-5-imidazolyl)-3-pyridinecarboxamide

The title compound was prepared from 6-chloronicotinonyl chloride and 5-amino-4-nitroimidazole as a brown solid as described in Example 1. $^1$H NMR (DMSO-$d_6$): 8.97–8.96 (m, 1H), 8.39–8.36 (m, 1H), 7.79–7.76 (m, 1H), 7.68 (s, 1H), 7.37 (s, 1H).

EXAMPLE 44

6-Chloro-N-(4-t-butyl-2-nitrophenyl)-3-pyridinecarboxamide

The title compound was prepared from 6-chloronicotinic chloride and 4-(t-butyl)-2-nitroaniline as a yellow solid as described in Example 1. $^1$H NMR (CDCl$_3$): 11.30 (s, 1H), 9.03 (d, J=2.1, 1H), 8.83 (d, J=9.0, 1H), 8.29 (d, J=2.7, 1H), 8.25–8.21 (m, 1H), 7.80–7.76 (m, 1H), 7.52 (d, J=8.4, 1H), 1.38 (s, 9H).

EXAMPLE 45

N-(4-Ethoxy-2-nitrophenyl)-5-pyrimidinecarboxamide

The title compound was prepared from pyrimidine-5-carboxylic acid and 4-ethoxy-2-nitroaniline as a yellow solid as described in Example 15. $^1$H NMR (CDCl$_3$): 11.16 (s, 1H), 9.43 (s, 1H), 9.32 (s, 2H), 8.81 (d, J=9.3, 1H), 7.76 (d, J=3.0, 1H), 7.34–7.27 (m, 1H), 4.12 (q, J=6.9, 2H), 1.47 (t, J=6.9, 3H).

EXAMPLE 46

N-(4-Ethoxy-2-nitrophenyl)-2-pyridinecarboxamide

The title compound was prepared from picolinic acid and 4-ethoxy-2-nitroaniline as a yellow solid as described in Example 15. $^1$H NMR (CDCl$_3$): 12.54 (s, 1H), 8.92 (d, J=9.3, 1H), 8.73 (d, J=3.9, 1H), 8.28 (d, J=6.9, 1H), 7.95–7.90 (m, 1H), 7.74 (d, J=3.0, 1H), 7.54–7.50 (m, 1H), 7.31–7.27 (m, 1H), 4.11 (q, J=6.9, 2H), 1.46 (t, J=6.9, 3H).

EXAMPLE 47

6-Chloro-N-(2-cyano-4,5-dimethoxyphenyl)-3-pyridinecarboxamide

The title compound was prepared from 6-chloronicotinoyl chloride and 2-amino-4,5-dimethoxybenzonitrile as a white solid as described in Example 1. $^1$H NMR (CDCl$_3$): 8.97 (d, J=2.7, 1H), 8.18–8.15 (m, 3H), 7.52 (d, J=8.4, 1H), 7.02 (s, 1H), 4.01 (s, 3H), 3.92 (s, 3H).

EXAMPLE 48

6-Chloro-N-(2-methoxycarbonyl-4,5-dimethoxyphenyl)-3-pyridinecarboxamide

The title compound was prepared from 6-chloronicotinoyl chloride and 2-amino-4,5-dimethoxybenzonic acid methyl ester as a light yellow solid as described in Example 1. $^1$H NMR (CDCl$_3$): 12.34 (s, 1H), 9.09 (d, J=2.4, 1H), 8.62 (s, 1H), 8.29–8.26 (m, 1H), 7.52 (s, 1H), 7.50 (d, J=8.4, 1H), 4.03 (s, 3H), 3.96 (s, 3H), 3.93 (s, 3H).

EXAMPLE 49

6-Chloro-N-(2-methylcarbonyl-4,5-methylenedioxyphenyl)-3-pyridinecarboxamide The title compound was prepared from 6-chloronicotinoyl chloride and 2-amino-4,5-methylenedioxyacetophenone as a light grey-yellow solid as described in Example 1. $^1$H NMR (CDCl$_3$): 9.09–9.08 (m, 1H), 8.55 (s, 1H), 8.30–8.27 (m, 1H), 7.50–7.47 (m, 1H), 7.35 (s, 1H), 6.10 (s, 2H), 2.64 (s, 3H).

EXAMPLE 50

6-(2,2,2-Triflouroethoxy)-N-(4ethoxy-2-nitrophenyl)-3-pyridinecarboxamide

The title compound was prepared from 6-(2,2,2-trifluoroethoxy)pyridine-3-carboxylic acid and 4-ethoxy-2-nitroaniline as a yellow solid as described in Example 15. $^1$H NMR (CDCl$_3$): 11.05 (s, 1H), 8.84–8.80 (m, 2H), 8.25–8.21 (m, 1H), 7.73 (d, J=3.0, 1H), 7.32–7.28 (m, 1H), 7.01 (d, J=8.7, 1H), 4.86 (q, J=8.4, 2H), 4.11 (q, J=6.9, 2H), 1.46 (t, J=6.9, 3H).

EXAMPLE 51

6-Chloro-N-(2,3-dinitro-4-methoxyphenyl)-3-pyridinecarboxamide

The title compound was prepared from 6-chloronicotinoyl chloride and 2,3-dinitro-4-methoxyaniline as a white solid as described in Example 1. $^1$H NMR (CDCl$_3$): 9.99 (s, 1H), 8.96 (d, J=2.4, 1H), 8.77 (d, J=9.3, 1H), 8.18–8.14 (m, 1H), 7.53 (d, J=9.0, 1H), 7.45 (d, J=9.3, 1H), 4.02 (s, 3H).

EXAMPLE 52

6-Chloro-N-(2-nitro-4,6-dimethylphenyl)-3-pyridinecarboxamide

The title compound was prepared from 6-chloronicotinoyl chloride and 2-nitro-4,6-dimethylaniline as a light yellow solid as described in Example 1. $^1$H NMR (CDCl$_3$): 9.09 (s, 1H), 8.97 (d, J=2.4, 1H), 8.22–8.18 (m, 1H), 7.60 (d, J=1.2, 1H), 7.50 (d, J=8.1, 1H), 7.42 (s, 1H), 2.43 (s, 3H), 2.35 (s, 3H).

EXAMPLE 53

4-Chloromethyl-N-(4-ethoxy-2-nitrophenyl)-benzoylamide

The title compound was prepared from 4-chloromethylbenzoyl chloride and 4-ethoxy-2-nitroaniline as a yellow solid as described in Example 1. $^1$H NMR (CDCl$_3$): 11.11 (s, 1H), 8.87 (d, J=9.3, 1H), 7.98 (d, J=8.4, 2H), 7.73 (d, J=3.0, 1H), 7.56 (d, J=8.4, 2H), 7.32–7.28 (m, 1H), 4.65 (s, 2H), 4.11 (q, J=6.9, 2H), 1.46 (t, J=6.9, 3H).

EXAMPLE 54

6-Chloro-N-(4,5-dimethoxy-2-nitrophenyl)-3-pyridinecarboxamide

The title compound was prepared from 6-chloronicotinoyl chloride and 4,5-dimethoxy-2-nitroaniline as a yellow solid as described in Example 1. $^1$H NMR (CDCl$_3$): 11.84 (s, 1H), 9.04 (d, J=1.8, 1H), 8.66 (s, 1H), 8.25–8.21 (m, 1H), 7.77 (s, 1H), 7.53 (d, J=8.7, 1H), 4.07 (s, 3H), 3.97 (s, 3H).

EXAMPLE 55

6-Chloro-N-(2-methoxy-5-pyridyl)-3-pyridinecarboxamide

The title compound was prepared from 6-chloronicotinoyl chloride and 5-amino-2-methoxypyridine as a pink solid as described in Example 1. $^1$H NMR (CDCl$_3$): 8.87 (d, J=2.1, 1H), 8.28 (d, J=3.0, 1H), 8.20–8.17 (m, 1H), 7.99–7.96 (m, 1H), 7.67 (s, 1H), 7.49 (d, J=8.7, 1H), 6.81 (d, J=8.7, 1H), 3.95 (s, 3H).

EXAMPLE 56

6-Chloro-N-(2-chloro-5-pyridyl)-3-pyridinecarboxamide

The title compound was prepared from 6-chloronicotinoyl chloride and 5-amino-2-chloropyridine as a white solid as described in Example 1. $^1$H NMR (CDCl$_3$): 8.89–8.84 (m, 1H), 8.52 (d, J=2.1, 1H), 8.27–8.23 (m, 1H), 8.21–8.17 (m, 1H), 7.83 (s, 1H), 7.53–7.50 (m, 1H), 7.39 (d, J=8.7, 1H).

EXAMPLE 57

6-Chloro-N-(4,6-dichloro-5-pyrimidyl)-3-pyridinecarboxamide

The title compound was prepared from 6-chloronicotinoyl chloride and 5-amino-4,6-dichloropyrimidine as a white solid as described in Example 1. $^1$H NMR (CDCl$_3$): 8.95 (d, J=2.4, 1H), 8.78 (s, 1H), 8.25–8.22 (m, 1H), 7.57 (s, 1H), 7.54 (d, J=8.4, 1H).

EXAMPLE 58

6-Cyano-N-(4-ethoxy-2-nitrophenyl)-3-pyridinecarboxamide

The title compound was prepared from 6-cyanonicotinic acid and 4-ethoxy-2-nitroaniline as a yellow solid as described in Example 15. $^1$H NMR (CDCl$_3$): 11.22 (s, 1H), 9.31–9.30 (m, 1H), 8.81 (d, J=9.3, 1H), 8.42–8.38 (m, 1H), 7.90–7.87 (m, 1H), 7.76 (d, J=3.0, 1H), 7.34–7.30 (m, 1H), 4.12 (q, J=6.9, 2H), 1.47 (t, J=6.9, 3H).

EXAMPLE 59

2-Methyl-N-(4-ethoxy-2-nitrophenyl)-3-furancarboxamide

The title compound was prepared from 2-methyl-3-furoic acid and 4-ethoxy-2-nitroaniline as an orange yellow solid as described in Example 15. $^1$H NMR (CDCl$_3$): 10.66 (s, 1H), 8.82 (d, J=9.3, 1H), 7.70 (d, J=3.0, 1H), 7.34 (d, J=1.8, 1H), 7.28–7.24 (m, 1H), 6.68 (d, J=1.8, 1H), 4.09 (q, J=6.9, 2H), 2.67 (s, 3H), 1.45 (t, J=6.9, 3H).

EXAMPLE 60

6-Chloro-N-(4-chloro-2-tifluoromethylphenyl)-3-pyridinecarboxamide

The title compound was prepared from 6-chloronicotinoyl chloride and 4-chloro-2-trifluoromethylaniline as a white solid as described in Example 1. $^1$H NMR (CDCl$_3$): 8.87 (d, J=2.7, 1H), 8.32 (d, J=8.7, 1H), 8.16–8.12 (m, 1H), 8.06 (bs, 1H), 7.82 (d, J=2.4, 1H), 7.53–7.50 (m, 1H), 7.12 (d, J=8.7, 1H).

EXAMPLE 61

4-Chloro-2-nitro-N-(6-chloro-3-pyridyl)-benzoylamide

The title compound was prepared from 4-chloro-2-nitrobenzoic acid and 5-amino-2-chloropyridine as a white solid as described in Example 15.

EXAMPLE 62

6-Chloro-N-(2-pyrazinyl)-3-pyridinecarboxamide

To a mixture of 6-chloronicotinoyl chloride (160 mg, 0.91 mmol), aminopyrazine (87 mg, 0.91 mmol) and THF (10 ml) was added triethylamine (0.25 ml, 1.82 mmol) and the mixture was stirred overnight at room temperature. The mixture was diluted with ethyl acetate (100 ml), wash with water (50 ml), saturated aqueous NaCl (50 ml), dried over anhydrous sodium sulfate and evaporated. The crude product was purified by column chromatography using hexane-:ethyl acetate (3:2) to give 8 mg (4% yield) of the title compound as yellow solid. $^1$H NMR (CDCl$_3$): 9.68 (d, J=1.2 Hz, 1H), 8.95 (d, J=2.7 Hz, 1H), 8.45 (d, J=2.7 Hz, 1H), 8.4 (bs, 1H), 8.33–8.32 (m, 1H), 8.23 (dd, J=2.4, 8.1 Hz, 1H), 7.53 (dd, J=0.6, 8.4 Hz, 1H).

EXAMPLE 63

4-Chloro-2-nitro-N-(6-methoxy-3-pyridyl)-benzoylamide

A mixture of cyanuric chloride (183 mg, 0.99 mmol) and 4-chloro-2-nitrobenzoic acid (200 mg, 0.99 mmol) in THF (5 ml) was stirred at room temperature for 30 minutes. To the mixture was added a solution of 5-amino-2-methoxy-pyridine (123 mg, 0.99 mmol) in THF (5 ml), followed by triethylamine (0.28 ml, 1.98 mmol). The mixture was stirred overnight at room temperature. It was diluted with 100 ml of hexane:ethyl acetate (1:1), wash with 2 N NaOH (50 ml), water (50 ml), followed by saturated aqueous NaCl (50 ml), dried over anhydrous sodium sulfate and evaporated. The crude product was purified by column chromatography using hexane:ethyl acetate (3:1) to give 16 mg (5% yield) of the title compound as a pink solid. $^1$H NMR (Acetone-d$_6$): 9.94 (s, 1H), 8.16 (d, J=1.8 Hz, 1H), 8.07–7.86 (m, 4H), 6.81 (d, J=9.3 Hz, 1H), 3.89 (s, 3H).

EXAMPLE 64

6-Chloro-N-(2-cyano-6-chloromethyl-4oxide-3-pyrazinyl)-3-pyridinecarboxamide

The title compound was prepared from 3-amino-6-(chloromethyl)-2-pyrazine carbonitrile 4-oxide (203 mg, 1.1 mmol) and 6-chloronicotinoyl chloride (200 mg, 1.1 mmol) and was obtained as an yellow solid as described in Example 62. $^1$H NMR (Acetone-d$_6$): 9.00 (s, 1H), 8.66 (s, 1H), 8.42 (dd, J=8.1, 2.1 Hz, 1H), 7.65 (d, J=8.1 Hz, 1H), 7.52 (s, 1H), 5.38 (s, 2H).

EXAMPLE 65

6-Chloro-N-(2-cyano-4-methylphenyl)-3-pyridinecarboxamide

A mixture of 2-amino-5-methyl-benzonitrile (80 mg, 0.61 mmol) and 6-chloronicotinoyl chloride (162 mg, 0.92 mmol) in anhydrous pyridine (5 ml) was refluxed for 4 hours. The mixture was diluted with 50 ml of hexane:ethyl acetate (1:1), wash with 2 N HCl (25 ml), water (25 ml), followed by saturated aqueous NaCl (25 ml), dried over anhydrous sodium sulfate, and evaporated. The crude product was purified by column chromatography using hexane-:ethyl acetate (2:1) to give 30 mg (18% yield) of the title compound as pale pink solid. $^1$H NMR (DMSO-d$_6$): 10.82 (s, 1H), 8.99 (d, J=2.4 Hz, 1H), 8.38 (dd, J=2.4, 8.1 Hz, 1H), 7.78–7.73 (m, 2H), 7.61–7.48 (m, 2H), 2.38 (s, 3H).

EXAMPLE 66

6-Chloro-N-(4-chloro-6-methyl-2-nitrophenyl)-3-pyridinecarboxamide

The title compound was prepared from 4-chloro-2-methyl-6-nitroaniline (204 mg, 1.09 mmol) and 6-chloronicotinoyl chloride (192 mg, 1.09 mmol) and obtained as a light yellow solid as described in Example 62. $^1$H NMR (CDCl$_3$): 9.13 (s, 1H), 8.96 (dd, J=0.6, 2.4 Hz, 1H), 8.20 (dd, J=2.7, 8.4 Hz, 1H), 7.93 (d, J=2.4 Hz, 1H), 7.59 (d, J=2.4 Hz, 1H), 7.51 (dd, J=0.6, 8.1 Hz, 1H), 2.38 (s, 3H).

EXAMPLE 67

4-Trifluoromethyl-N-(4-ethoxy-2-nitrophenyl)-3-pyridinecarboxamide

A mixture of 4-(trifluoromethyl)pyridine-3-carboxylic acid (100 mg, 0.52 mmol), 4-ethoxy-2-nitroaniline (94.7 mg, 0.52 mmol), and 1-(3-dimethylamino-propyl)-3-ethylcarbodiimide hydrochloride (199.3 mg, 1.04 mmol) in THF (5 ml) was refluxed overnight. The mixture was cooled to room temperature, diluted with 100 ml of hexane:ethyl acetate (1:1), wash with 2 N NaOH (50 ml), water (50 ml), saturated aqueous NaCl (50 ml), dried over anhydrous sodium sulfate and evaporated. The crude product was purified by column chromatography using hexane:ethyl acetate (2:1) to give 17.3 mg (9.4% yield) of the title compound as yellow solid. $^1$H NMR (CDCl$_3$): 10.48 (s, 1H), 9.01–8.96 (m, 2H), 8.74 (d, J=9.3 Hz, 1H), 7.74–7.69 (m, 2H), 7.32 (dd, J=3.0, 9.3 Hz, 1H), 4.13 (q, J=6.9 Hz, 2H), 1.48 (t, J=6.9 Hz, 3H).

EXAMPLE 68

4-Bromomethyl-3-nitro-N-(6-chloro-3-pyridyl)-benzoylamide

A mixture of 4-bromomethyl-3-nitrobenzoic acid (169 mg, 0.65 mmol), 5-amino-2-chloropyridine (83 mg, 0.65 mmol) and 1-ethyl-3-(3-dimethylaminopropyl)carbodiimide hydrochloride (210 mg) in THF (10 ml) was refluxed for 24 h. The mixture was cooled to room temperature and diluted with hexane:ethyl acetate (1:1, 100 ml), washed with water (50 ml), 2 N HCl (50 ml), brine (50 ml) and dried over anhydrous sodium sulfate. The solution was concentrated in vacuo to give a yellow solid which was washed with dichloromethane and dried to give 68 mg (28%) of the title compound. $^1$H NMR (DMSO-d$_6$): 10.91 (s, 1H), 8.77 (d, J=2.1 Hz, 1H), 8.63 (s, 1H), 8.31 (d, J=8.1 Hz, 1H), 8.24 (dd, J=2.4, 8.7 Hz, 1H), 7.96 (d, J=8.1 Hz, 1H), 7.56 (d, J=8.7 Hz, 1H), 5.11 (s, 2H).

EXAMPLE 69

6-Chloromethyl-N-(4-ethoxy-2-nitrophenyl)-3-pyridinecarboxamide

A) Methyl 6-chloromethylnicotinate: A mixture of methyl 6-methylnicotinate (2.3 g, 15.2 mmol) and N-chlorosuccinimide (4.6 g, 34 mmol) in chloroform was refluxed for 24 h to give 1.3 g of the title compound as a white solid.

B) 6-Chloromethylnicotinic acid: A mixture of methyl 6-chloromethylnicotinate (1.3 g, 6.5 mmol) in 2 N HCl (40 ml) was refluxed for 5 h. The mixture was cooled to room temperature to give 1.1 g of the title compound as a tan solid.

C) 6-Chloromethyl-N-(4-ethoxy-2-nitrophenyl)-3-pyridinecarboxamide: A mixture of 6-chloromethylnicotinic acid (155 mg, 0.69 mmol), 4-ethoxy-2-nitroaniline (146 mg), 1-ethyl-3-(3-dimethylaminopropyl)carbodiimide hydrochloride (238 mg) and pyridine in THF (10 ml) was refluxed for 17 h. The mixture was cooled to room temperature, diluted with hexane:ethyl acetate (1:1, 100 ml), washed with water (50 ml), 2 N HCl (50 ml), brine (50 ml) and dried over anhydrous sodium sulfate. The solution was concentrated in vacuo and the product was purified by column chromatography using hexane:ethyl acetate (3:1) to give the title compound as a yellow solid (30 mg). $^1$H NMR (CDCl$_3$): 11.14 (s, 1H), 9.18 (m, 1H), 8.84 (d, J=9.3 Hz, 1H), 8.30 (dd, J=2.4, 8.1 Hz, 1H), 7.75 (d, J=3.0 Hz, 1H), 7.68 (d, J=8.4 Hz, 1H), 7.31 (dd, J=3.0, 9.3 Hz, 1H), 4.76 (s, 2H), 4.12 (m, 2H), 1.47 (t, J=7.1 Hz, 3H).

EXAMPLE 70

N-(4-Ethoxy-2-nitrophenyl)-3-furancarboxamide

The title compound was prepared from 3-furoic acid and 4-ethoxy-2-nitroaniline as a yellow solid as described in Example 15. $^1$H NMR (DMSO-d$_6$): 10.25 (s, 1H), 8.36 (d, J=2.4, 1H), 7.83–7.81 (m, 1H), 7.53–7.47 (m, 2H), 7.35–7.31 (m, 1H), 6.94 (d, J=2.4, 1H), 4.12 (q, J=6.9, 2H), 1.35 (t, J=6.9, 3H).

EXAMPLE 71

Identification of N-(4-methoxy-2-nitrophenyl)-3-pyridinecarboxamide and Analogs as Caspase Cascade Activators and Inducers of Apoptosis in Solid Tumor Cells Human breast cancer cell lines T47D and ZR75-1 were grown according to media component mixtures designated by American Type Culture Collection +10% FCS (Invitrogen Corporation, Life Technologies Division), in a 5% $CO_2$ –95% humidity incubator at 37° C. T47D and ZR75–1 cells were maintained at a cell density between 30 and 80% confluency at a cell density of 0.1 to $0.6 \times 10^6$ cells/ml. Cells were harvested at 600xg and resuspended at $0.65 \times 10^6$ cells/ml into appropriate media +10% FCS. An aliquot of 45 μl of cells was added to a well of a 96-well microtiter plate containing 5 μl of a 10% DMSO in RPMI-1640 media solution containing 1.6 to 100 μM of N-(4-methoxy-2-nitrophenyl)-3-pyridinecarboxamide or other test compound (0.16 to 10 μM final). An aliquot of 45 μl of cells was added to a well of a 96-well microtiter plate containing 5 μl of a 10% DMSO in RPMI-1640 media solution without test compound as the control sample. The samples were mixed by agitation and then incubated at 37 C. for 24 h in a 5% $CO_2$ –95% humidity incubator. After incubation, the samples were removed from the incubator and 50 μl of a solution containing 20 μM of N-(Ac-DEVD)-N'-ethoxycarbonyl-R110 (SEQ ID NO: 1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 μg/ml lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}.$$

The activity of caspase cascade activation was determined by the ratio of the net RFU value for N-(4-methoxy-2-nitrophenyl)-3-pyridinecarboxamide or other test compound to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

| | Caspase Activity and Potency | | | |
|---|---|---|---|---|
| | T47D | | ZR75-1 | |
| Example # | Ratio | EC50 (nM) | Ratio | EC50 (nM) |
| 1 | 8.9 | 2970 | 3.6 | 729 |
| 2 | 7.8 | 587 | 5.8 | 329 |
| 3 | Inactive | Inactive | 2.1 | 4620 |
| 4 | Inactive | Inactive | 3.2 | 4030 |
| 5 | Inactive | Inactive | Inactive | Inactive |
| 6 | Inactive | Inactive | Inactive | Inactive |
| 7 | 8.1 | 593 | 2.7 | 230 |
| 8 | 5.0 | 153 | 6.3 | 77 |
| 9 | 5.4 | 920 | 5.0 | 488 |
| 10 | Inactive | Inactive | Inactive | Inactive |
| 11 | Inactive | Inactive | Inactive | Inactive |
| 12 | Inactive | Inactive | Inactive | Inactive |
| 13 | Inactive | Inactive | Inactive | Inactive |
| 14 | Inactive | Inactive | Inactive | Inactive |
| 15 | Inactive | Inactive | Inactive | Inactive |
| 16 | Inactive | Inactive | Inactive | Inactive |
| 17 | Inactive | Inactive | Inactive | Inactive |
| 18 | 3.0 | 6750 | 5.1 | 3840 |
| 19 | 2.7 | 3550 | 3.8 | 6880 |
| 20 | Inactive | Inactive | Inactive | Inactive |
| 21 | Inactive | Inactive | 2.3 | 4670 |
| 22 | 7.6 | 466 | 6.6 | 295 |
| 23 | 7.2 | 608 | 9.9 | 171 |
| 24 | Inactive | Inactive | Inactive | Inactive |
| 25 | 5.8 | 345 | 6.6 | 133 |
| 26 | 5.5 | 42 | 3.2 | 20 |
| 27 | Inactive | Inactive | Inactive | Inactive |
| 28 | 2.4 | 7330 | 5.1 | 4510 |
| 29 | 5.8 | 1800 | 6.4 | 1000 |
| 30 | Inactive | Inactive | Inactive | Inactive |

Thus, N-(4-methoxy-2-nitrophenyl)-3-pyridinecarboxamide (Example 29) and analogs are identified as potent caspase cascade activators and inducer of apoptosis in solid tumor cells.

EXAMPLE 72

Figure 1B:
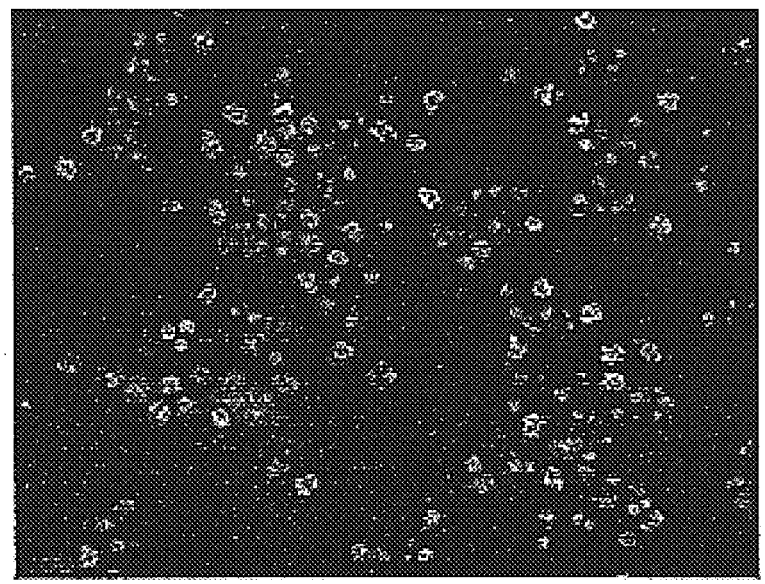

N-(4-Methoxy-2-nitrophenyl)-3-pyridinecarboxamide Induces Nuclear Fragmentation in Jurkat Cells The ability of N-(4-methoxy-2-nitrophenyl)-3-pyridinecarboxamide to induce nuclear fragmentation was tested by treatment of Jurkat cells with the test compound followed by staining of the nucleus with Sytol6, a fluorescent DNA dye (Molecular Probes, Eugene, Oreg.). The nuclei of Jurkat cells treated with vehicle control (DMSO) are seen to be round with dispersed chromatin that is moderately stained with Sytol6 (FIG. 1A). In contrast, Jurkat cells treated with 5 μM of N-(4-methoxy-2-nitrophenyl)-3-pyridinecarboxamide for 24 h have shrunken and fragmented nuclei (FIG. 1B), which is a hallmark of caspase-mediated apoptosis. These results corroborate the caspase induction assays by showing that N-(4-methoxy-2-nitrophenyl)-3-pyridinecarboxamide can induce a key cellular marker of apoptosis.

EXAMPLE 73

Figure 2:
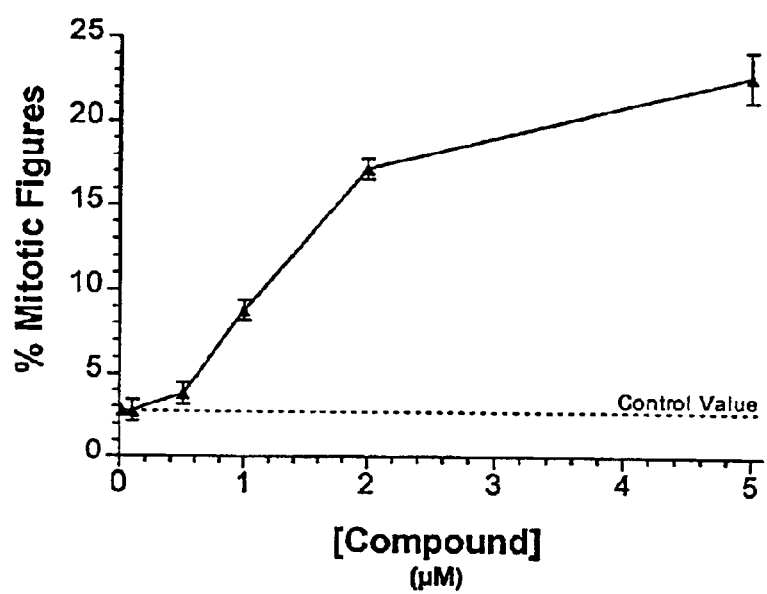
FIG. 2 is a graph showing mitotic arrest in Jurkat cells treated for 6 h with different concentrations of N-(4-methoxy-2-nitrophenyl)-3-pyridinecarboxamide.

N-(4-methoxy-2-nitrophenyl)-3-pyridinecarboxamide Induces Mitotic Arrest in Jurkat Cells Jurkat cells were incubated with a range of concentrations of N-(4-methoxy-2-nitrophenyl)-3-pyridinecarboxamide (0.02 μM to 5 μM) for 6 h under normal growth conditions; control cultures were treated with DMSO vehicle. The cells were then treated for 20 min. with 800 nM Syto 16 (Molecular Probes, Eugene, OR). Cytospin preparations were then prepared and the samples were viewed by fluorescent microscopy using a fluorescein filter set. For each concentration of test compound, the number of mitotic figures were counted and expressed as a percentage of the total number of cells. Three fields from each condition were evaluated and the mean and SEM were calculated and plotted as a function of drug concentration (FIG. 2). The results show that N-(4-methoxy-2-nitrophenyl)-3-pyridinecarboxamide is an effective inducer of mitotic arrest in Jurkat cells up to a concentration of 5 µM.

EXAMPLE 74

Figure 3A:
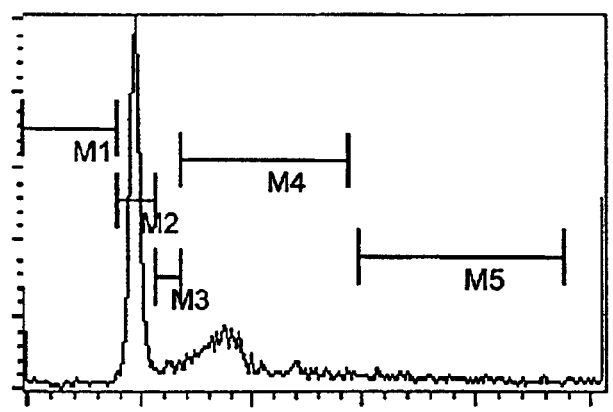
FIGS. 3A–B are graphs showing drug induced cell cycle arrest and apoptosis in T47D cells.
Figure 3B:
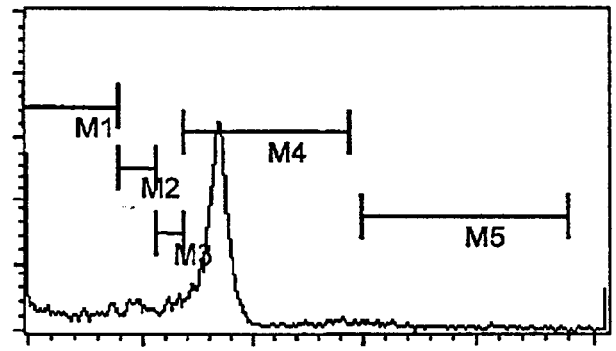
Figure 4A:
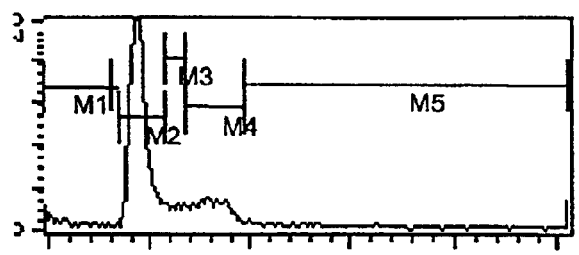
FIGS. 4A–B are graphs showing drug induced cell cycle arrest and apoptosis in T47D cells.
Figure 4B:
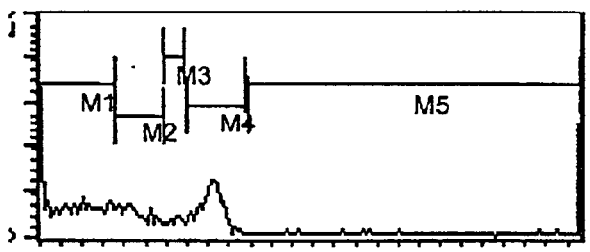

Treatment with N-(4-Methoxy-2-nitrophenyl)-3-pyridinecarboxamide or 6-Chloro-N-(4-ethoxy-2-nitrophenyl)-3-pyridinecarboxamide Leads to Cell Cycle Arrest and Apoptosis in Solid Tumor Cell Line T47D, a breast cancer cell line, was maintained and harvested as described in Example 71. $1 \times 10^6$ cells were treated with 10 µM of N-(4-methoxy-2-nitrophenyl)-3-pyridinecarboxamide or 6-chloro-N-(4-ethoxy-2-nitrophenyl)-3-pyridinecarboxamide for 48 h at 37° C. As a control, cells were also incubated with equivalent amount of solvent as control (DMSO). Cells were harvested at 1,200 rpm and washed twice with 5 mM EDTA/PBS. Cells were then resuspended in 300 µl EDTA/PBS and 700 µl of 100% ethanol, vortexed and incubated at room temperature for 1 h. Samples were spun down at 1,200 rpm for 5 min and the supernatant was removed. A solution containing 100 µg/ml of propidium iodide and 1 mg/ml of RNAse A (fresh) was added to the samples and incubated for 1 h at room temperature. Samples were then transferred to 12×75 mm polystyrene tubes and analyzed on a flow cytometer. All flow cytometry analyses were performed on FACScalibur (Becton Dickinson) using Cell Quest analysis software. On the x-axis is plotted the fluorescence intensity and on the y-axis is plotted the number of cells with that fluorescence intensity. The T47D control cell population profile is seen in FIG. 3A and the increase in G2/M DNA content (M4) cells that is seen when treated with N-(4-methoxy-2-nitrophenyl)-3-pyridinecarboxamide at 10 µM is seen in FIG. 3B. An increase in the sub-diploid DNA content of cells (marker M1 region, FIG. 3) is also seen to increase from 2% to 25% with compound treatment. The sub-diploid amount of DNA (M1) is indicative of apoptotic cells which have undergone DNA degradation or fragmentation. In cells treated with 6-chloro-N-(4-ethoxy-2-nitrophenyl)-3-pyridinecarbox-amide, a more potent analog, at 1 µM (FIG. 4B), the accumulation of T47D cells in the G2/M phase (M4) is similarly seen. In addition, the sub-G1 population of cells with reduced DNA content (M1) indicative of apoptosis is seen to increase substantially over control cells (FIG. 4A), indicating cell cycle arrest and induction of apoptosis by treatment with N-(4-methoxy-2-nitrophenyl)-3-pyridinecarboxamide and its more potent analog 6-chloro-N-(4-ethoxy-2-nitrophenyl)-3-pyridinecarboxamide.

EXAMPLE 75

6-Chloro-N-(4-ethoxy-2-nitrophenyl)-3-pyridinecarboxamide Inhibits the Proliferation of Solid Tumor HeLa Cell Line HeLa cells were grown according to media component mixtures designated by American Type Culture Collection +10% FCS (Invitrogen Corporation, Life Technologies Division), in a 5% $CO_2$ –95% humidity incubator at 37° C. In a well of a 96 well plate, 30,000 cells were seeded and treated with compound at the indicated concentrations for 48 hr in a 5% $CO_2$–95% humidity incubator at 37° C. Control wells were treated with the same amount of solvent (DMSO) as the compound samples. After the indicated treatment time, the supernatant was removed to a sterile culture tube and the wells washed with phosphate buffered saline, and the adherent cells trypsinized for 5 min. The trypsinzed cells were added to the culture supernatant, cells were collected (1,200 rpm, 10 min), washed with phosphate buffered saline, and resuspended in fresh media. The cells were counted for trypan blue negative cells, and the cells were diluted with fresh media to 1,000 cells/ml. To a well of a 24-well plate, 0.1 ml of the cell suspension was added along with 1 ml of fresh media (cell suspensions were passed through a 22G needle several times just before plating to form single cell suspensions). Plates are incubated in a 5% $Co_2$–95% humidity incubator at 37° C. for 5–7 days. Colonies are counted when the sizes reached greater than 50 cells per colony. Cells are washed with phosphate buffered saline, fixed with 100% methanol for 15 min, and then stained with 0.5% gentian violet for 15 min. Colonies are rinsed with water and the colonies counted and the fraction surviving expressed as the percentage of the number of control colonies.

Figure 5:
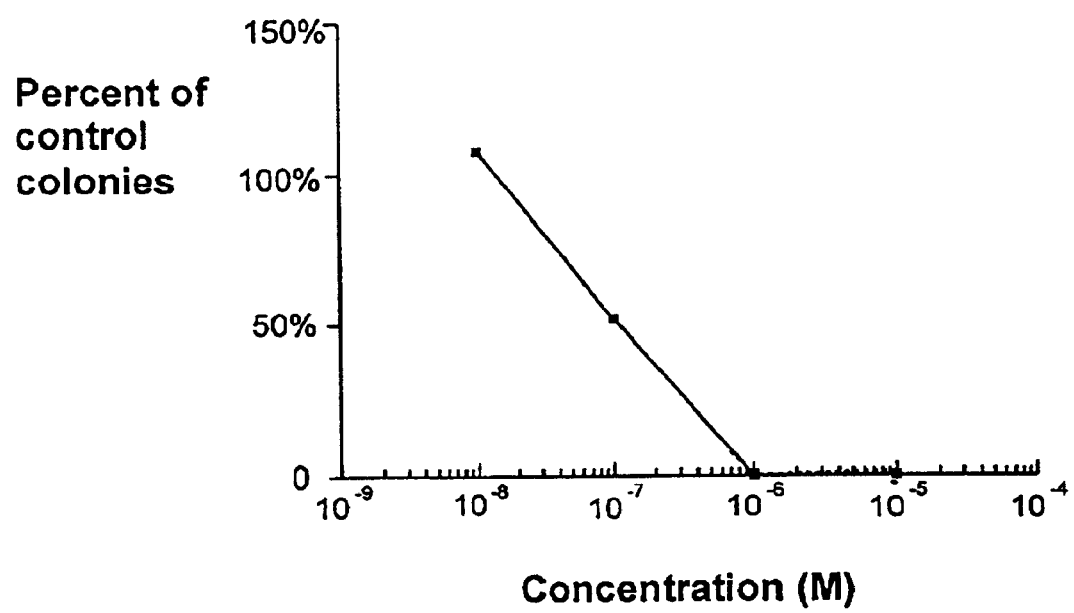
FIG. 5 is a graph showing inhibition of proliferation of HeLa cells treated for 48 h with different concentrations of 6-chloro-N-(4-ethoxy-2-nitrophenyl)-3-pyridinecarboxamide.

The results showed that after a 48 hr treatment, 6-chloro-N-(4-ethoxy-2-nitrophenyl)-3-pyridinecarboxamide inhibits the ability of HeLa cells to continue to proliferate and inhibited their colony forming ability with an $IC_{50}$ of about 100 nM (FIG. 5)

Having now fully described this invention, it will be understood by those of ordinary skill in the art that the same may be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound of Formula III:

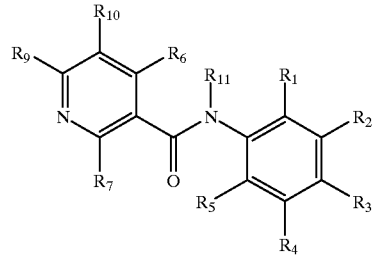

(III)

or a pharmaceutically acceptable salt or prodrug thereof, wherein $R_1$ and $R_5$ are independently selected from the group consisting of hydrogen, hydroxy, alkyl, alkoxy, halogen, $NO_2$, cyano, haloalkyl, haloalkoxy, amino and aminoalkyl, provided that at least one of $R_1$ and $R_5$ is selected from the group consisting of $NO_2$, cyano, alkyl and haloalkyl;

$R_2$ and $R_4$ are independently selected from the group consisting of hydrogen, hydroxy, halogen, cyano, haloalkyl, haloalkoxy, amino and aminoalkyl;

$R_3$ is propyl, isopropyl, butyl, sec-butyl, tert-butyl, 3-pentyl, hexyl, octyl, Cl, F, haloalkyl, alkoxy, arylalkoxy, cyano, haloalkyloxy, amino or aniinoalkyl;

$R_6$ is hydrogen, hydroxy, alkyl, $NO_2$, cyano, haloalkyl, haloalkyloxy, amino or aminoalkyl;

R₇ is hydrogen, hydroxy, alkyl, NO₂, cyano, haloalkyl, haloalkyloxy, amino or aminoalkyl;

R₉ is hydroxy, alkyl, halogen, NO₂, haloalkyl, alkoxy, cyano, haloalkyloxy, amino or aminoalkyl;

R₁₀ is hydrogen, hydroxy, alkyl, Cl, F, NO₂, cyano, haloalkyl, haloalkyloxy, amino or aminoalkyl; and R₁₁ is hydrogen, alkyl or haloalkyl;

wherein said prodrug is:
  a) an ester of a carboxylic acid containing compound of Formula III obtained by condensation with a C₁₋₄ alcohol;
  b) an ester of a hydroxyl group containing compound of Formula III obtained by condensation with a C₁₋₄ carboxylic acid, C₃₋₆ dioic acid or anhydride thereof;
  c) an imine of an amine group containing compound of Formula III obtained by condensation with a C₁₋₄ aldehyde or ketone; or
  d) an acetal or ketal of at least one of the R₁₋₁₀ hydroxy containing groups obtained by condensation with chloromethyl methyl ether or chloromethyl ethyl ether.

2. The compound of claim 1, wherein said compound is selected from the group consisting of:

6-Chloro-N-(4,5-difluoro-2-nitrophenyl)-3-pyridinecarboxamide;
6-Chloro-N-(3-bromo-4-methoxy-6-nitrophenyl)-3-pyridinecarboxamide;
5,6-Dichloro-N-(4-methoxy-2-nitrophenyl)-3-pyridinecarboxamide;
6-Chloro-N-(2-methyl-4-methoxyphenyl)-3-pyridinecarboxamide;
6-Chloro-N-(4-ethoxy-2-nitrophenyl)-N-methyl-3-pyridinecarboxamide;
6-Chloro-N-(2-cyano-4,5-dimethoxyphenyl)-3-pyridinecarboxamide;
6-Chloro-N-(4-chloro-2-trifluoromethylphenyl)-3-pyridinecarboxamide;
6-Chloro-N-(4-chloro-2-cyanophenyl)-3-pyridinecarboxamide;
6-Chloro-N-(2,4-dimethyl-6-nitrophenyl)-3-pyridinecarboxamide;
6-Chloro-N-(3,4-dimethoxy-6-nitrophenyl)-3-pyridinecarboxamide; and
6-Chloro-N-(2-cyano-4-methylphenyl)-3-pyridinecarboxamide.

3. The compound of claim 1, wherein said compound is of Formula IV:

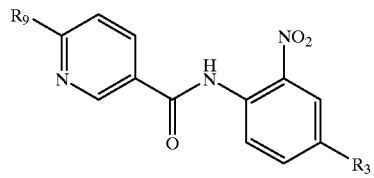

(IV)

or a pharmaceutically acceptable salt or prodrug thereof.

4. The compound of claim 3, wherein said compound is selected from the group consisting of:

6-Chloro-N-(4-methoxy-2-nitrophenyl)-3-pyridinecarboxamide;
6-Chloro-N-(4-ethoxy-2-nitrophenyl)-3-pyridinecarboxamide;
6-Chloro-N-(4-methoxy-2-nitrophenyl)-1-N-oxide-3-pyridinecarboxamide;
6-Chloro-N-(4-chloro-2-nitrophenyl)-3-pyridinecarboxamide;
6-Fluoro-N-(4-ethoxy-2-nitrophenyl)-3-pyridinecarboxamide;
6-Chloro-N-(4-trifluoromethyl-2-nitrophenyl)-3-pyridinecarboxamide;
6-Chloro-N-(2-nitro-4-trifluoromethoxy]phenyl)-3-pyridinecarboxamide;
6-Chloro-N-(4-benzyloxy-2-nitrophenyl)-3-pyridinecarboxamide;
6-Methyl-N-(4-ethoxy-2-nitrophenyl)-3-pyridinecarboxamide;
6-Chloro-N-(4-cyano-2-nitrophenyl)-3-pyridinecarboxamide;
6-(2,2,2-Trifluoroethoxy)-N-(4-ethoxy-2-nitrophenyl)-3-pyridinecarboxamide;
6-Dimethylamino-N-(4-ethoxy-2-nitrophenyl)-3-pyridinecarboxamide;
6-Chloro-N-(4-t-butyl-2-nitrophenyl)-3-pyridinecarboxamide; and
6-Trifluoromethyl-N-(4-ethoxy-2-nitrophenyl)-3-pyridinecarboxamide.

5. A compound selected from the group consisting of 6-Chloro-N-(2,4-dimethyl-6-nitrophenyl)-3-pyridinecarboxamide, 6-Chloro-N-(4-methyl-2-nitrophenyl)-3-pyridinecarboxamide, and 4-Chloromethyl-N-(4-ethoxy-2-nitrophenyl)-3-pyridinecarboxamide.

6. A pharmaceutical composition, comprising the compound of any one of claims 1–4, and a pharmaceutically acceptable carrier.

7. A method of treating a disorder responsive to the induction of apoptosis in an animal suffering therefrom, comprising administering to a mammal in need of such treatment an effective amount of a compound of Formula

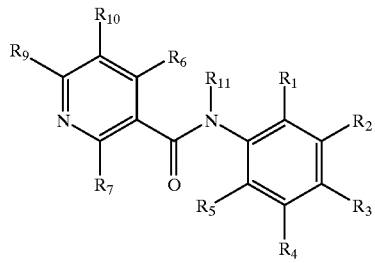

(III)

or a pharmaceutically acceptable salt or prodrug thereof, wherein

R₇ and R₉–R₁₀ are independently hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, beteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, hydroxy, thiol, acyloxy, azido, alkoxy, aryloxy, arylalkoxy, carbonylaínido, alkyithiol, —NH₂, —NHR₁₅ or —NR₁₅R₁₆;

R₁ is halo, aryl, fused aryl, carbocyclic, fused carbocyclic, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido, alkyithiol, —NH$_2$, —NHR$_{15}$, or —NR$_{15}$R$_{16}$;

R$_2$–R$_5$ are hydrogen, halo, aryl, fused aryl, carbocyclic, fused carbocyclic, alkyl, alkenyl, alkynyl, arylalkyl, arylalkenyl, arylalkynyl, heteroarylalkyl, heteroarylalkenyl, heteroarylalkynyl, carbocycloalicyl, heterocycloalkyl, hydroxyalkyl, nitro, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido, alkyithiol, —NH$_2$, —NHR$_{15}$ or —NR$_{15}$R$_{16}$;

R$_6$ is hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, thiol, acyloxy, azido, alkoxy, alkoxycarbonyl, aryloxy, arylalkoxy, carboxy, carbonylamido, alkyithiol, —NH$_2$, —NHR$_{15}$ or —NR$_{15}$R$_{16}$, wherein R$_{15}$ and R$_{16}$ are independently optionally substituted C$_{1-10}$ alkyl, heterocyclic or heteroaryl groups; and R$_{11}$ is hydrogen; or alkyl, cycloalkyl, aryl or heteroaryl, each of which is optionally substituted;

wherein said disorder responsive to the induction of apoptosis is a cancer selected from the group consisting of Hodgkin's disease, non-Hodgkin's lymphoma, acute lymphocytic leukemia, chronic lyruphocytic leukemia, carcinoma, cervical carcinoma chronic granulocytic leukemia, acute granulocytic leukemia, and hairy cell leukemia; and wherein said prodrug is:

a) an ester of a carboxylic acid containing compound of Formula III obtained by condensation with a C$_{1-4}$ alcohol;

b) an ester of a hydroxyl group containing compound of Formula III obtained by condensation with a C$_{1-4}$ carboxylic acid, C$_{3-6}$ dioic acid or anhydride thereof;

c) an imine of an amine group containing compound of Formula III obtained by condensation with a C$_{1-4}$ aldehyde or ketone; or d) an acetal or ketal of at least one of the R$_{1-10}$ hydroxy containing groups obtained by condensation with chloromethyl methyl ether or chloromethyl ethyl ether.

8. The method of claim 7, wherein R$_1$ and R$_2$, or R$_2$ and R$_3$, or R$_3$ and R$_4$, or R$_4$ and R$_5$ are taken together to form an optionally substituted carbocycle.

9. The method of claim 8, wherein R$_1$ and R$_2$, or R$_2$ and R$_3$, or R$_3$ and R$_4$, or R$_4$ and R$_5$ are taken together to form —(CH$_2$)$_3$—, —(CH$_2$)$_4$—, or —CH=CH—CH=CH—, wherein the carbocycle is optionally substituted.

10. The method of claim 7, wherein R$_6$, R$_7$ and R$_{10}$ are independently hydrogen or fluoro.

11. The method of claim 7, wherein R$_1$ is nitro.

12. The method of claim 7, wherein R$_2$, R$_4$, and R$_5$ are independently hydrogen or fluoro.

13. The method of claim 7, wherein said compound is selected from the group consisting of:

N-(4-Methyl-2-nitrophenyl)-3-pyridinecarboxamide;

N-(4-Ethoxy-2-nitrophenyl)-3-pyridinecarboxamide;

N-(4-Methoxy-2-nitrophenyl)-3-pyridinecarboxanlide;

6-Chloro-N-(4,5-difluoro-2-nitrophenyl)-3-pyridinecarboxaniide;

6-Chloro-N-(3-bromo-4-methoxy-6-nitrophenyl)-3-pyridinecarboxamide;

5,6-Dichloro-N-(4-methoxy-2-nitrophenyl)-3-pyridinecarboxaniide;

6-Chloro-N-(2-methyl-4-methoxyphenyl)-3-pyridinecarboxamide;

6-Chloro-N-(4-ethoxy-2-nitrophenyl)-N-methyl-3-pyridinecarboxamide;

6-Chloro-N-(2-cyao-4,5-dimethoxyphenyl)-3-pyridinecarboxamide;

6-Chloro-N-(4-chloro-2-cyanophenyl)-3-pyridinecarboxamide;

6-Chloro-N-(2,4-dimethyl-6-nitrophenyl)-3-pyridinecarboxamide;

6-Chloro-N-(3,4-dimethoxy-6-nitrophenyl)-3-pyridinecarboxamide;

6-Chloro-N-(2-cyano-4-methylphenyl)-3-pyridinecarboxamide;

6-Chloro-N-(4-chloro-2-methyl-6-nitrophenyl)-3-pyridinecarboxamide, and

4-Trifluoromethyl-N-(4-ethoxy-2-nitrophenyl)-3-pyridinecarboxamide.

14. The method of claim 7, wherein said compound is of Formula IV:

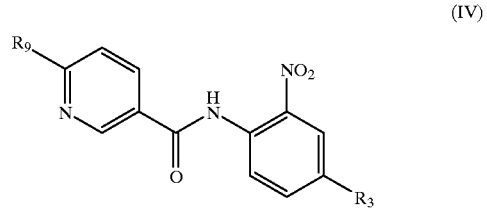

(IV)

or a pharmaceutically acceptable salt or prodrug thereof.

15. The method of claim 14, wherein said compound is selected from the group consisting of:

6-Chloro-N-(4-methoxy-2-nitrophenyl)-3-pyridinecarboXafllide;

6-Chloro-N-(4-ethoxy-2-nitrophenyl)-3-pyridinecarboxanlide;

6-Chloro-N-(4-methyl-2-nitrophenyl)-3-pyridinecarboxainide;

6-Chloro-N-(4-mcthoxy-2-nitrophenyl)-1-N-oxide-3-pyridinecarboxamide;

6-Chloro-N-(4-chloro-2-nitrophenyl)-3-pyridinecarboxaflhide;

6-Fluoro-N-(4-ethoxy-2-nitrophenyl)-3-pyridinecarbOxaflhide;

6-Chloro-N-(4-fluoro-2-nitrophenyl)-3-pyridinecarboxaflhide;

6-Chloro-N-(4-benzyloxy-2-nitrophenyl)-3-pyridinecarboxamide;

6-Methyl-N-(4-ethoxy-2-nitrophenyl)-3-pyridinecarboxaniide;

6-Chloro-N-(4-cyano-2-nitropbenyl)-3-pyridinecarboxaniide;

6-(2,2,2-Trifluoroethoxy)-N-(4-ethoxy-2-nitrophenyl)-3-pyridinecarboxamide;

6-Dimethylamino-N-(4-ethoxy-2-nitrophenyl)-3-pyridinecarboxamide;
6-Chloro-N-(4-t-butyl-2-nitrophenyl)-3-pyridinecarboxamide;
6-Trifluoromethyl-N-(4-ethoxy-2-nitrophenyl)-3-pyridinecarboxamide; and
6-Chloromethyl-N-(4-ethoxy-2-nitrophenyl)-3-pyridinecarboxaniide.

16. A method for treating cancer, comprising administering to an animal in need of such treatment an effective amount of a compound of Formula m:

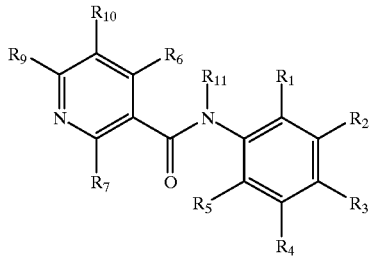

(III)

or a pharmaceutically acceptable salt or prodrug thereof, wherein
  $R_7$ and $R_9$–$R_{10}$ are independently hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido, alkylthiol, —$NH_2$, —$NHR_{15}$ or —$NR_{15}R_{16}$;
  $R_1$–$R_5$ are hydrogen, halo, haloalkyl, haloalkoxy, aryl, fused aryl, carbocyclic, fused carbocyclic, alkyl, alkenyl, alkynyl, arylalkyl, arylalkenyl, arylalkynyl, heteroarylalkyl, heteroarylalkenyl, heteroarylailcynyl, carbocycloalkyl, heterocycloalkyl, hydroxyalkyl, nitro, aminoalkyl, cyano, cyanoalkyl, acyl, acylamido, hydroxy, thiol, acyloxy, azido, alkoxy, alkoxycarbonyl, aryloxy, arylalkoxy, carboxy, carbonylamido, alkyithiol, —$NH_2$, —$NHR_{15}$ or —$NR_{15}R_{16}$;
  $R_6$ is hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, thiol, acyloxy, azido, alkoxy, alkoxycarbonyl, aryloxy, arylalkoxy, carboxy, carbonylamido, alkyithiol, —$NH_2$, —$NHR_{15}$ or —$NR_{15}R_{16}$, wherein
    $R_{15}$ and $R_{16}$ are independently optionally substituted $C_{1-10}$ alkyl, heterocyclic or heteroaryl groups; and
  $R_{11}$ is hydrogen; or alkyl, cycloalkyl, aryl or heteroaryl, each of which is optionally substituted;
wherein said cancer is selected from the group consisting of Hodgkin's disease, non-Hodgkin's lymphoma, acute lymphocytic leukemia, chronic lymphocytic leukemia, breast carcinoma, cervical carcinoma, chronic granulocytic leukemia, acute granulocytic leukemia, and hairy cell leukemia; and wherein said prodrug is:
  a) an ester of a carboxylic acid containing compound of Formula III obtained by condensation with a $C_{1-4}$ alcohol;
  b) an ester of a hydroxyl group containing compound of Formula III obtained by condensation with a $C_{1-4}$ carboxylic acid, $C_{3-6}$ dioic acid or anhydride thereof;
  c) an imine of an amine group containing compound of Formula III obtained by condensation with a $C_{1-4}$ aldehyde or ketone; or
  d) an acetal or ketal of at least one of the $R_{1-10}$ hydroxy containing groups obtained by condensation with chloromethyl methyl ether or chloromethyl ethyl ether.

17. The method of claim 16, wherein said compound is of Formula IV:

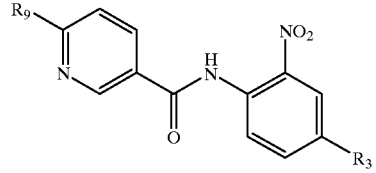

(IV)

or a pharmaceutically acceptable salt or prodrug thereof.

18. A method for the treatment of drug resistant cancer, comprising administering to an animal in need of such treatment an effective amount of a compound of the Formula III:

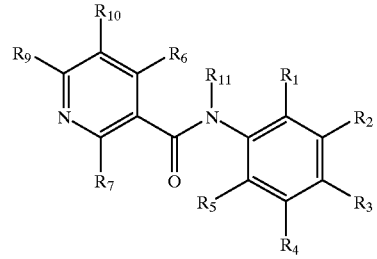

(III)

or a pharmaceutically acceptable salt or prodrug thereof, wherein:
  $R_7$ and $R_9$–$R_{10}$ are independently hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aniinoalkyl, cyano, cyanoalkyl, acyl, acylamido, hydroxy, thiol, acyloxy, azido, alkoxy, alkoxycarbonyl, aryloxy, arylalkoxy, carboxy, carbonylamido, alkylthiol, —$NH_2$, —$NHR_{15}$ or —$NR_{15}R_{16}$;
  $R_1$–$R_5$ are hydrogen, halo, haloalkyl, haloalkoxy, aryl, fused aryl, carbocyclic, fused carbocyclic, alkyl, alkenyl, alkynyl, arylalkyl, arylalkenyl, arylalkynyl, heteroarylallcyl, heteroarylalkenyl, heteroarylalkynyl, carbocycloalkyl, heterocycloalkyl, hydroxyalkyl, nitro, aminoalkyl, cyano, cyanoalkyl, acyl, acylaniido, hydroxy, thiol, acyloxy, azido, alkoxy, alkoxycarbonyl, aryloxy, arylalkoxy, carboxy, carbonylamido, alkyithiol, —$NH_2$, —$NHR_{15}$ or —$NR_{15}R_{16}$;

$R_6$ is hydrogen, halo, haloalkyl, haloalkoxy, aryl, fused aryl, carbocyclic, fused carbocyclic, a heterocyclic group, fused heterocyclic, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, aminoalkyl, cyano, cyanoalkyl, acyl, acylamido, thiol, acyloxy, azido, alkoxy, alkoxycarbonyl, aryloxy, arylalkoxy, carboxy, carbonylamido, alkyithiol, —$NH_2$, —$NHR_{15}$ or —$NR_{15}R_{16}$, wherein $R_{15}$ and $R_{16}$ are independently optionally substituted $C_{1-10}$ alkyl, heterocyclic or heteroaryl groups; and $R_{11}$ is hydrogen; or alkyl, cycloalkyl, aryl or heteroaryl, each of which is optionally substituted;

wherein said cancer is selected from the group consisting of Hodgkin's disease, non-Hodgkin's lymphoma, acute lymphocytic leukemia, chronic lymphocytic leukemia, breast carcinoma, cervical carcinoma, chronic granulocytic leukemia, acute granulocytic leukemia, and hairy cell leukemia; and wherein said prodrug is:

a) an ester of a carboxylic acid containing compound of Formula III obtained by condensation with a $C_{1-4}$ alcohol;

b) an ester of a hydroxyl group containing compound of Formula III obtained by condensation with a $C_{1-4}$ carboxylic acid, $C_{3-6}$ dioic acid or anhydride thereof;

c) an imine of an amine group containing compound of Formula III obtained by condensation with a $C_{1-4}$ aldehyde or ketone; or d) an acetal or ketal of at least one of the $R_{1-10}$ hydroxy containing groups obtained by condensation with chloromethyl methyl ether or chloromethyl ethyl ether.

19. The method of any one of claims 7, 16, and 18 wherein optional substituents on the alkyl or heteroaryl group of $R_{15}$ and $R_{16}$ or the alkyl, aryl, or heteroaryl group of $R_{11}$ include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_{6-C10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

20. The method of claim 18, wherein said compound is of Formula IV:

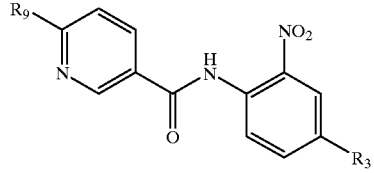

(IV)

or a pharmaceutically acceptable salt or prodrug thereof.

21. The method of claim 16 or 18, additionally comprising treating said animal with radiation-therapy.

22. The method of claim 16 or 18, wherein said compound is administered after the surgical treatment of said animal for cancer.

23. The method of claim 7, wherein said disorder is breast carcinoma.

24. The method of claim 7, wherein said disorder is cervical carcinoma.

25. The method of claim 7, wherein said disorder is Hodgkin's disease, non-Hodgkin's lymphoma, acute lymphocytic leukemia, chronic lymphocytic leukemia, multiple myeloma, chronic granulocytic leukemia, acute granulocytic leukemia, or hairy cell leukemia.

* * * * *

UNITED STATES PATENT AND TRADEMARK OFFICE
CERTIFICATE OF CORRECTION

PATENT NO.   : 6,794,397 B2
DATED        : September 21, 2004
INVENTOR(S)  : Cai et al.

It is certified that error appears in the above-identified patent and that said Letters Patent is hereby corrected as shown below:

Column 40,
Line 65, please delete "aniinoalkyl" and replace therein with -- aminoalkyl --.

Column 41,
Lines 40-41, please delete which read "6-Chloro-N-(2,4-dimethyl-6-nitrophenyl)-3-pyridinecarboxamide;".
Line 43, please delete "and".
Line 45, please delete "." and insert therein -- ; and --.
Lines 45 and 46, please insert the following between --6-Chloro-N-(4-chloro-2-methyl-6-nitrophenyl)-3-pyridinecarboxamide. --.

Column 42,
Lines 6 and 7, please insert --6-Chloro-N-(4-fluoro-2-nitrophenyl)-3-pyridinecarboxamide; --.
Line 9, please delete "trifluoromethoxy]phenyl" and insert therein -- trifluoromethoxylphenyl --.
Line 28, please insert the following between "pyridinecarboxamide," and "and" -- 4-Trifluoromethyl-N-(4-ethoxy-2-nitrophenyl)-3-pyridinecarboxamide, --.
Line 36, please delete "Formula" and insert therein -- Formula III: --.
Line 62, please delete "carbonylainido, alkyithiol," and insert therein -- carbonylamido, alkylthiol, --.

Column 43,
Line 11, please delete "carbocycloalicyl" and insert therein -- carbocycloalkyl --.
Lines 15 and 25, please delete "alkyithiol" and insert therein -- alkyithiol --.
Line 34, please delete "lyruphocytic" and insert therein -- lymphocytic --.
Lines 34-35, please insert --breast-- between "leukemia," and "carcinoma".

Column 44,
Lines 2 and 47, please delete "pyridinecarboxanlide" and insert therein -- pyridinecarboxamide --.
Lines 4, 8, 61 and 63, please delete "pyridinecarboxaniide" and insert therein -- pyridinecarboxamide --.
Line 13, please delete "cyao" and insert therein -- cyano --.
Line 45, please delete "pyridinecarboXafllide" and insert therein -- pyridinecarboxamide --.
Line 49, please delete "pyridinecarboxainide" and insert therein -- pyridinecarboxamide --.
Line 50, please delete "mcthoxy" and insert therein -- methoxy --.

UNITED STATES PATENT AND TRADEMARK OFFICE
CERTIFICATE OF CORRECTION

PATENT NO. : 6,794,397 B2
DATED : September 21, 2004
INVENTOR(S) : Cai et al.

It is certified that error appears in the above-identified patent and that said Letters Patent is hereby corrected as shown below:

Column 44 (cont'd),
Lines 53 and 57, please delete "pyridinecarboxaflhide" and insert therein
-- pyridinecarboxamide --.
Line 55, please delete "pyridinecarbOxaflhide" and insert therein
-- pyridinecarboxamide --.
Line 62, please delete "nitropbenyl" and insert therein -- nitrophenyl --.

Column 45,
Line 8, please delete "pyridinecarboxaniide" and insert therein -- pyridinecarboxamide --.
Line 11, please delete "m" and insert therein -- III --.
Line 41, please delete "heteroarylailcynyl" and insert therein -- heteroarylalkynyl --.
Lines 46 and 55, please delete "alkyithiol" and insert therein -- alkylthiol --.

Column 46,
Line 13, please delete "chioromethyl" and insert therein -- chloromethyl --.
Line 54, please delete "aniinoalkyl" and insert therein -- aminoalkyl --.
Line 61, please delete "heteroarylallcyl" and insert therein -- heteroarylalkyl --.
Line 63, please delete "acylaniido" and insert therein -- acylamido --.
Line 66, please delete "alkyithiol" and insert therein -- alkylthiol --.

Column 47,
Line 9, please delete "alkyithiol" and insert therein -- alkylthiol --.

Column 48,
Line 4, please delete "$C_6$-$C_{10}$" and insert therein -- $C_6$-$C_{10}$ --.

Signed and Sealed this

Fifth Day of April, 2005

JON W. DUDAS
*Director of the United States Patent and Trademark Office*